(12) United States Patent
Verhoeven et al.

(10) Patent No.: US 12,129,065 B2
(45) Date of Patent: Oct. 29, 2024

(54) METHOD AND SYSTEM FOR REPROCESSING REUSABLE MEDICAL INSTRUMENTS

(71) Applicant: Log10 B.V., Eindhoven (NL)

(72) Inventors: Franciscus Maria Verhoeven, Eindhoven (NL); Paul Herman Maria Pessers, Eindhoven (NL); Theo Alex Eduard Van Der Leij, Eindhoven (NL); Jolande Wilhelmina Bakker-Van De Kerkhof, Eindhoven (NL)

(73) Assignee: LOG10 B.V., Eindhoven (NL)

( * ) Notice: Subject to any disclaimer, the term of this patent is extended or adjusted under 35 U.S.C. 154(b) by 713 days.

(21) Appl. No.: 16/982,731

(22) PCT Filed: Mar. 22, 2019

(86) PCT No.: PCT/NL2019/050179
§ 371 (c)(1),
(2) Date: Sep. 21, 2020

(87) PCT Pub. No.: WO2019/182449
PCT Pub. Date: Sep. 26, 2019

(65) Prior Publication Data
US 2021/0002013 A1    Jan. 7, 2021

(30) Foreign Application Priority Data

Mar. 23, 2018  (NL) ...................................... 2020655
Mar. 11, 2019  (NL) ...................................... 2022713

(51) Int. Cl.
*B65B 55/02*      (2006.01)
*A61B 50/00*      (2016.01)
(Continued)

(52) U.S. Cl.
CPC ............ *B65B 55/027* (2013.01); *A61B 50/33* (2016.02); *A61L 2/07* (2013.01); *A61L 2/202* (2013.01);
(Continued)

(58) Field of Classification Search
CPC ....................................................... A61L 2/07
See application file for complete search history.

(56) References Cited

U.S. PATENT DOCUMENTS 3,247,957 A    4/1966 Kemble
2005/0224382 A1    10/2005 Raynal-Olive et al.
(Continued)

FOREIGN PATENT DOCUMENTS

CN    101219072 A    7/2008
CN    106999616 A    8/2017
(Continued)

OTHER PUBLICATIONS

JP 2018524128 A_translation.*
(Continued)

*Primary Examiner* — Kevin Joyner
*Assistant Examiner* — Changru Chen
(74) *Attorney, Agent, or Firm* — Pillsbury Winthrop Shaw Pittman, LLP

(57) ABSTRACT

A method and system for reprocessing a reusable medical instrument. The method includes providing a container including a tray and a lid, the tray having an opening for inserting therethrough the medical instrument into an inner space of the tray, and the lid being arranged for closing the opening. The method includes inserting the container into a decontamination device, inside the decontamination device decontaminating the tray, the lid and the medical instrument while the lid is positioned away from the opening. The method includes, inside the decontamination device, a con-
(Continued)

tainer handler of the decontamination device closing the container by closing the lid onto the tray for closing the opening, and removing the closed container containing the decontaminated medical instrument from the decontamination device.

18 Claims, 13 Drawing Sheets

(51) Int. Cl.
    *A61B 50/33*     (2016.01)
    *A61L 2/07*     (2006.01)
    *A61L 2/20*     (2006.01)
    *A61L 2/26*     (2006.01)
    *B08B 3/08*     (2006.01)
    *A61B 90/70*     (2016.01)
    *A61B 90/92*     (2016.01)
    *A61B 90/94*     (2016.01)
    *A61B 90/98*     (2016.01)

(52) U.S. Cl.
    CPC ................. *A61L 2/26* (2013.01); *B08B 3/08* (2013.01); *A61B 2050/006* (2016.02); *A61B 90/70* (2016.02); *A61B 90/92* (2016.02); *A61B 90/94* (2016.02); *A61B 90/98* (2016.02); *A61L 2202/17* (2013.01); *A61L 2202/182* (2013.01); *A61L 2202/24* (2013.01)

(56) References Cited

U.S. PATENT DOCUMENTS

| | | |
|---|---|---|
| 2006/0096877 A1 | 5/2006 | Khajavi et al. |
| 2008/0150722 A1 | 6/2008 | Jackson |
| 2008/0236631 A1 | 10/2008 | Lin et al. |
| 2010/0065456 A1 | 3/2010 | Junk et al. |
| 2010/0154353 A1 | 6/2010 | Cesa et al. |
| 2011/0262301 A1* | 10/2011 | Ghelman ............... A61L 2/07 422/26 |
| 2014/0077435 A1 | 3/2014 | Powell |
| 2015/0306259 A1 | 10/2015 | Deutschle et al. |
| 2017/0258951 A1 | 9/2017 | Kemp et al. |

FOREIGN PATENT DOCUMENTS

| | | | |
|---|---|---|---|
| DE | 102012200331 A1 * | 7/2013 | ........... A61C 19/002 |
| EP | 1787731 A2 * | 5/2007 | ............... A61L 2/04 |
| EP | 3139968 A1 | 3/2017 | |
| GB | 2525846 A | 11/2015 | |
| JP | 50-65297 U | 6/1975 | |
| JP | H11-267190 A | 10/1999 | |
| JP | 2018524128 A * | 8/2018 | ............... A61L 9/14 |
| WO | WO-2014159696 A1 * | 10/2014 | ............... A61L 2/07 |
| WO | 2015/171590 A1 | 11/2015 | |
| WO | WO-2016039647 A2 * | 3/2016 | ............. A61B 50/30 |

OTHER PUBLICATIONS

DE 102012200331 A1_translation.*
Notice of Reasons for Refusal dated Dec. 23, 2022, issued in corresponding Japanese Patent Application No. 2021-500773 with English machine translation (6 pgs.).
International Search Report dated Jul. 7, 2019 issued in corresponding International Application No. PCT/NL2019/050179 (4 pgs.).
Written Opinion of the International Searching Authority dated Jul. 7, 2019 issued in corresponding International Application No. PCT/NL2019/050179 (5 pgs.).
Notice of Second Review Observations, dated Jul. 27, 2024, issued in corresponding Chinese Patent Application No. 201980034507.X, with English translation (23 pgs.).

\* cited by examiner

METHOD AND SYSTEM FOR REPROCESSING REUSABLE MEDICAL INSTRUMENTS

CROSS-REFERENCE TO RELATED APPLICATIONS

This application is the U.S. National Stage of PCT/NL2019/050179, filed Mar. 22, 2019, which claims priority to: Netherlands Patent Application No. 2020655, filed Mar. 23, 2018, and Netherlands Patent Application No. 2022713, filed Mar. 11, 2019, the entire contents of each of which are herein incorporated by reference in their entireties.

FIELD OF THE INVENTION

The invention relates to reprocessing of reusable medical instruments, such as dental instruments.

BACKGROUND TO THE INVENTION

Reusable medical instruments are instruments that health care providers can reuse to diagnose and/or treat multiple patients. Examples of reusable medical instruments include medical instruments used in dental care, such as scalpels, syringes, scopes, mirrors, drills, burs, discs, hand pieces, excavators, turbines, files, reamers, etc.

When used on patients, reusable instruments become soiled and contaminated with blood, tissue and other biological debris such as microorganisms. To avoid any risk of infection by a contaminated instrument, reusable instruments undergo reprocessing, a process to decontaminate, e.g. clean and disinfect and/or sterilize, them. Reprocessing results in a medical instrument that can be safely used more than once in the same patient, or in more than one patient. Adequate reprocessing of reusable medical instruments is vital to protecting patient safety.

SUMMARY OF THE INVENTION

It is an object to provide a system and a method that render the task of decontaminating a medical instrument less cumbersome, less time-consuming and/or less expensive. More in general, it is an object to provide a method and system for reprocessing a reusable medical instrument.

Thereto, according to an aspect is provided a method for reprocessing a reusable medical instrument. The method includes providing a container including a tray and a lid. The tray includes one or more supports supporting the medical instrument. The tray includes an opening for inserting therethrough the medical instrument into an inner space of the tray. The lid is arranged for closing the opening. The method includes inserting the container into a decontamination device. The method includes, inside the decontamination device decontaminating the tray, the lid and the medical instrument while the lid is positioned away from the opening. The method includes, inside the decontamination device, a container handler of the decontamination device closing the container by closing the lid onto the tray for closing the opening. The method can include sealing the container inside the decontamination device, such as in a clean zone, such as a decontamination chamber, of the decontamination device. The method includes removing the closed container containing the decontaminated medical instrument from the decontamination device. Hence, the container is closed, and optionally hermetically sealed, when the tray, the lid and the medical instrument have been decontaminated. The container is closed inside the decontamination device, such as in the clean zone, such as the decontamination chamber, of the decontamination device. Hence, the decontaminated container can be closed around the decontaminated medical instrument in the clean zone of the device. Thus, decontamination of the content of the container, i.e. the medical instrument, can easily be provided. Also, the lid being positioned away from the opening during decontamination allows for easy access of the inner space and the medical instrument during decontamination.

The container is preferably such that when positioned in a position for normal use (e.g. placed on a table top) the opening extends substantially horizontally. Preferably, the medical instruments are positioned inside the container in a lying down position, when the container is in the position for normal use. Preferably, the medical instruments are positioned (substantially) horizontally in the container when the container is in the position for normal use.

Optionally, the method includes maintaining the tray in a position with the opening extending in an upright plane while decontaminating. Hence, the plane in which the opening extend is upright, e.g. substantially vertical, e.g. vertical. This allows easy access during decontamination. This also allows easy dripping off of liquids used during decontamination. The lid(s) can also be maintained extending in such upright plane. The lid(s) can e.g. be displaced from the opening(s) in a direction away from the opening(s), e.g. along an axis extending perpendicular through the plane(s) in which the opening(s) extend. Thus, the lid(s) can be maintained close to the tray, while still allowing good access to the inner space of the tray for decontamination.

Optionally, the medical instrument(s) to be decontaminated are maintained in an upright position during decontamination. For generally elongate medical instruments, in the upright position, the main axis of elongation of the instrument is upright, such as substantially vertical. When the medical instruments are positioned (substantially) horizontally in the container when the container is in the position for normal use, the medical tools can also be maintained in the upright position when maintaining the tray in a position with the opening extending in an upright plane. Then, liquids easily drip off the medical instruments. Also, the contact area of the instrument with the supports can be minimized. Especially when using jets during decontamination, and/or when using ultrasonic cleaning, the points of contact will change during decontamination, thus allowing full decontamination of the instrument.

Optionally, the container is inserted into the decontamination device in a non-sealed state of the container. Hence, the non-sealed container can be entered into the decontamination device, and the sealed container exits the decontamination device. Processing a container inserted into the decontamination device in a sealed state could require additional and/or more complex processing of the container. If the container is non-sealed when inserted into the decontamination device, operation of the decontamination device can be independent of how well a user closed the container before insertion thereof into the device. Hence, for processing a container inserted into the decontamination device in the non-sealed state a less complex decontamination device can suffice.

In the non-sealed state, the container is open to outside air. Hence, in the non-sealed state microbes and other decontamination can enter the container. In the sealed state, a microbial barrier is formed preventing microbes from entering the inner space. Hence, the sealed container provides protection against microbial contamination when released from the decontamination device. Optionally, in the sealed state the container is hermetically closed.

Optionally, during the step of decontaminating the container is subsequently held in a first chamber and a second chamber. Optionally, the method includes performing washing in the first chamber of the decontamination device, and performing sterilizing in the second chamber of the decontamination device.

Optionally, the decontaminating includes one or more of rinsing, washing, disinfecting, sterilizing, and drying. Optionally, the decontaminating includes ultrasonic cleaning. The washing can include washing at a low temperature, e.g. at about 37° C., to avoid coagulation of blood. Alternatively, or additionally, the washing can include washing at a high temperature, e.g. at 50-100° C., e.g. at about 73° C. It is possible that the decontaminating steps are performed in the two chambers, or in more chambers. For example, each decontaminating step can be performed in a dedicated chamber.

Optionally, the first chamber and the second chamber are positioned with their respective main planes of extension substantially parallel. Herein, the main plane of extension indicates the directions of the two largest dimensions of the chamber. For example, for a chamber having a length exceeding a width, and the width exceeding a height, the largest dimensions are the length and the width. Hence, the main plane of extension is the plane defined by the length and the width of said chamber. When the first chamber and the second chamber are positioned with their respective main planes of extension substantially parallel, they occupy a compact volume. Hence, a compact build of the decontamination device is possible. When the decontamination device includes more than two chambers, preferably the more than two chambers are positioned with their respective main planes of extension substantially parallel.

Optionally, the container is closed while being moved from the first chamber to the second chamber. Hence, the container is open in the first chamber for processing, is moved from the first chamber to the second chamber in a closed state, and is re-opened in the second chamber for further processing. This provides the advantage that the inside of the container is not contaminated while outside the first or second chamber. This also provides the advantage that the decontamination device is not contaminated while the container is outside the first or second chamber. When the decontamination device includes more than two chambers, preferably the container is closed while being moved from one chamber to the next chamber.

Optionally, the step of closing includes hermetically closing the container. Optionally, the method further including reducing gas pressure inside the container prior to closing the container and maintaining said reduced gas pressure inside the container after removing the closed container from the decontamination device. Thus, the decontaminated medical instrument can be stored under reduced gas pressure until next use. The container can include a tamper evidence feature arranged for being in a first state when the reduced gas pressure is present inside the container, and in a second state when ambient pressure is present inside the container. Thus, it can easily be determined whether the container is still in the reduced gas pressure state in which it was released by the decontamination device or not. The gas used for filling the container can be air, e.g. filtered using a high-efficiency particulate air (HEPA) filter. The gas can also be an inert gas such as nitrogen.

Optionally, the method includes inside the decontamination device applying a label to the container. Optionally, the method includes labelling, e.g. using a labelling unit of the decontamination device, the container with a label representative of the performed decontamination. The label can e.g. be a sticker or can be printed onto the container. Hence it is possible to determine the decontamination performed on the instrument from the label. The label can include information on the performed decontamination, e.g. a code representative of performed process steps. The label can also include information representative of a location in a database where information on the performed decontamination is stored. The label can include information representative of a date and time of decontamination.

Optionally, in the non-sealed state a perforation of the lid, and/or tray provides an open connection from an inner space of the container to ambient air. Optionally, the method including closing the perforation with the label. The label can hermetically seal the perforation. Hence, removal of the label can break the hermetic seal. The label can e.g. be a paper and/or plastic label. Also the user may verify the existence of the hermetic seal just prior to opening of the container by observing the sound of the container filling with air through the perforation upon removal of the label.

Optionally, the container includes a further lid. The tray can have a further opening, preferably opposite the first opening, the further lid being arranged for closing the further opening. The method can include, inside the decontamination device, decontaminating the tray, the lid, the further lid and the medical instrument while the lid is positioned away from the opening and the further lid is positioned away from the further opening. The method can include, inside the decontamination device, the container handler closing the lid onto the tray for closing the opening, and closing the further lid onto the tray for closing the further opening. It will be appreciated that when decontaminating the container with the lid and the further lid, it is also possible to decontaminate the tray, the lid, the further lid and the medical instrument while only one of the lid and the further lid is positioned away from the opening or the further opening, respectively.

Optionally, the opening spans substantially the entire cross sectional area in top plan view of the tray. The opening can e.g. be larger than 80%, preferably 90%, of the cross sectional area in top plan view of the tray. Side walls of the tray, such as substantially vertical side walls, can define the opening.

Optionally, the further opening spans substantially the entire cross sectional area in top plan view of the tray. The further opening can e.g. be larger than 80%, preferably 90%, of the cross sectional area in top plan view of the tray. Side walls of the tray, such as substantially vertical side walls, can define the further opening. The tray can be substantially tubular. The tubular tray can have a length (in the direction from the first opening to the second opening) that is smaller than a dimension orthogonal to the length. The one or more supports of the tray can be arranged for holding one or more medical instrument between the opening and the further opening. The one or more supports can be arranged for locking the instrument(s) in the tray to prevent the instrument(s) from falling out of the tray, e.g. regardless of the orientation of the tray.

Optionally, the step of inserting includes inserting the container into the decontamination device while the lid, and the optional further lid, is closed onto the tray. Thus a closed container, preferably containing one or more medical instruments to be decontaminated, can be inserted into the decontamination device. Hence, the user can collect the medical devices after use on a patient in a container, close the container, and present the closed container at the decontamination device for reprocessing.

Optionally, the method includes, inside the decontamination device, removing the lid from the opening, and optionally removing the further lid from the further opening. Thus, the closed container containing the medical devices to be decontaminated can be inserted into the decontamination device, the decontamination device opening the container for good access to the medical instrument during decontamination.

Optionally, the method includes the container handler gripping the container by the tray, by the lid, and optionally by the optional further lid. Hence, the container handler can effectively open and/or close the container as desired.

It will be appreciated that it is also possible to present an open container at the decontamination device. It is e.g. possible to present trays and lids separately to the decontamination device, e.g. in separate stacks and/or separate entry ports.

Optionally, the instrument is a dental instrument. The dental instruments can e.g. be scalpels, syringes, scopes, mirrors, drills, burs, discs, handpieces, excavators, turbines, files, reamers, (plastic) re-usables, disposables, prosthetics, implants, 3D printed implants, inserts, measuring devices, spreaders etc.

Optionally, the method includes the decontamination device reading decontamination instructions from a machine readable identification of the container. The decontamination device can then perform the decontamination process according to the read instructions.

Optionally, the decontamination device stores data representative of the decontamination process of a particular container in a record in a memory. Thus, it is possible to retrieve the data representative of the decontamination process.

Optionally, the decontamination device monitors a decontamination history of a container. It is for instance possible that the decontamination device warns that a certain container has not been decontaminated for a predetermined period of time, e.g. approaching, coinciding with, or exceeding an expiration time of the previous decontamination process. Thus, the decontamination device may e.g. warn that decontamination of a predetermined container has expired, and e.g. request said container to be presented at the decontamination device for renewed decontamination.

According to an aspect is provided a system for reprocessing a reusable medical instrument. The system includes a decontamination device and a container. The container includes a tray and a lid. The tray includes one or more supports for supporting one or more medical instruments. The tray includes an opening for inserting therethrough the one or more medical instruments into an inner space of the tray. The lid is arranged for closing the opening. The decontamination device includes an entrance for inserting the container into the decontamination device. The decontamination device includes a container handler arranged for holding the container in the decontamination device. The decontamination device includes a decontamination unit arranged for decontaminating the tray, the lid and the medical instrument. The decontamination device includes an exit for removing the closed container containing the decontaminated medical instrument from the decontamination device. The container handler is arranged for holding the lid positioned away from the opening while decontaminating. The container handler is arranged for closing the container by closing the lid onto the tray after decontamination.

Optionally, the container handler is arranged for maintaining the tray in a position with the opening extending in an upright plane, and optionally the further opening extending in a further upright plane, while decontaminating.

Optionally, the container is arranged to be inserted into the decontamination device while the container is in a non-sealed state.

Optionally, the decontamination device includes a first chamber and a second chamber. The container handler can be arranged for transporting the container from the first chamber to the second chamber. The decontamination device can be arranged for performing a first decontaminating, such as washing and/or disinfecting, in the first chamber. The decontamination device can be arranged for performing a second decontaminating, such as sterilizing, in the second chamber. The container handler can be arranged for closing the container after the first decontaminating, transporting the closed container from the first chamber to the second chamber, and opening the container in the second chamber for performing the second decontaminating. It is also possible that the decontamination device includes more than two chambers.

Optionally, the first chamber and the second chamber are positioned with their respective main directions of extension substantially parallel.

Optionally, the system is arranged for closing the container while moving it from the first chamber to the second chamber.

Optionally, the system includes a labelling unit arranged for applying a label to the container. Optionally, in the non-sealed state a perforation of the lid and/or tray provides an open connection from an inner space of the container to ambient air. Optionally, the labelling unit is arranged for closing the perforation with the label.

Optionally, the container includes a further lid. The tray can have a further opening, preferably opposite the first opening. The container handler can be arranged for holding the further lid positioned away from the further opening while decontaminating. The container handler can be arranged for closing the container by closing the further lid onto the tray after decontamination.

Optionally, the entrance is arranged for receiving the container while the lid, and the optional further lid, is closed onto the tray.

Optionally, the container handler is arranged for removing the lid from the opening, and optionally removing the further lid from the further opening, prior to decontamination.

Optionally, the container handler is arranged for gripping the container by the tray, by the lid, and optionally by the optional further lid. Optionally, the lid includes a tab or rim arranged for being gripped by the container handler. Optionally, the further lid includes a tab or rim arranged for being gripped by the container handler. Optionally, the tray includes a tab or rim arranged for being gripped by the container handler. Optionally, one or more of the lid, the further lid, and the tray includes a centering tab for centering the lid, the further lid or the tray, respectively, relative to the container handler.

Optionally, the lid includes one or more recesses or protrusions, arranged for cooperating with one or more corresponding protrusions or recesses, respectively, of a tray of another container, for stacking the containers.

Optionally, the lid includes one or more recesses or protrusions, arranged for cooperating with one or more corresponding protrusions or recesses, respectively, of a further lid of another container, for stacking the containers.

Optionally, the lid includes a geometry arranged for allowing stable positioning on the tray in an upside-down manner. Thus, in a simple manner a decontaminated workspace can be provided for preparing the decontaminated instrument(s).

Optionally, the decontamination unit is arranged for one or more of rinsing, washing, disinfecting, sterilizing, and drying. Rinsing can be performed using water, such as cold water for preventing coagulation of blood. Washing can be performed using water. The washing can include washing at a low temperature, e.g. at about 37° C., to avoid coagulation of blood. Alternatively, or additionally, the washing can include washing at a high temperature, e.g. at 50-100° C., e.g. at about 73° C. The washing can include using water, e.g. using a detergent. Disinfecting can be performed using a disinfectant. Sterilizing can be performed using steam. Preferably, sterilizing is performed using a gaseous sterilizer such as ozone. Drying can be performed using, e.g. hot, air. It is possible that the decontaminating steps are performed in the two chambers, or in more chambers. For example, each decontaminating step can be performed in a dedicated chamber. The decontamination device can include one or more of a rinsing chamber, a washing chamber, a disinfecting chamber, a drying chamber, and a sterilizing chamber. The decontamination device can include a first washing chamber and a second washing chamber. The first washing chamber can be arranged for washing at the low temperature. The second washing chamber can be arranged for washing at the high temperature.

Optionally, the decontamination unit is arranged for ultrasonically cleaning the instruments. The decontamination device can include an ultrasonic cleaning chamber.

Optionally, the decontamination system is arranged for closing the container such that a microbial barrier is formed preventing microbes from entering the inner space. Optionally, the decontamination system is arranged for hermetically closing the container. Optionally, the system includes a pump for reducing a gas pressure inside the container prior to closing the container.

Optionally, the system includes a reader arranged for reading decontamination instructions from a machine readable identification of the container.

According to an aspect is provided a container of the system.

According to an aspect is provided a container holding at least one reprocessed medical instrument, including
 a tray including an inner space, one or more supports supporting the at least one medical instrument, and a first opening at a first side for inserting a medical instrument into the inner space through the first opening; and
 a first lid closing the first opening;
 wherein the at least one reprocessed medical instrument has been sterilized.

The container holding the sterilized reprocessed instrument in a simple manner provides the sterilized reprocessed instrument to a user.

According to an aspect is provided a container holding at least one reprocessed medical instrument, including:
 a tray including an inner space, one or more supports supporting the at least one medical instrument, and a first opening at a first side for inserting a medical instrument into the inner space through the first opening; and
 a first lid closing the first opening;
 wherein the at least one reprocessed medical instrument has been disinfected, but not sterilized.

The container holding the disinfected but not sterilized reprocessed instrument in a simple manner provides the disinfected but not sterilized reprocessed instrument to a user. It has been found that disinfected but not sterilized reprocessed medical instruments are generally not packaged in the closed container. Hence, contamination of the disinfected but not sterilized medical instruments is a real risk.

Preferably, the container holding the disinfected but not sterilized reprocessed instrument is hermetically sealed, e.g. containing a pressure below ambient pressure inside the container. Hence, disinfection quality of the disinfected but not sterilized reprocessed medical instrument can easily be guaranteed.

According to an aspect is provided a reprocessing container for holding a reusable medical instrument. The container includes a tray. The tray includes an inner space. The tray includes one or more supports for supporting one or more medical instruments. The tray includes a first opening at a first side for inserting a medical instrument into the inner space through the first opening. The container includes a first lid for closing the first opening.

In view of all of the containers described hereinabove, the following options and features are noted.

Optionally, the container is such that when positioned in a position for normal use (e.g. placed on a table top) the opening extends substantially horizontally. Preferably, the medical instruments are positioned inside the container in a lying down position, when the container is in the position for normal use. Preferably, the medical instruments are positioned (substantially) horizontally in the container when the container is in the position for normal use.

Optionally, the first opening spans substantially the entire cross sectional area in top plan view of the tray. The first opening can e.g. be larger than 80%, preferably 90%, of the cross sectional area in top plan view of the tray. Side walls of the tray, such as substantially vertical side walls, can define the first opening.

Optionally, the container further includes a second opening at a second side opposite to the first side, and a second lid for closing the second opening. Hence, cleaning of the inside of the container and the instruments contained therein, e.g. in the decontamination device, can be greatly enhanced.

Optionally, the second opening spans substantially the entire cross sectional area in top plan view of the tray. The second opening can e.g. be larger than 80%, preferably 90%, of the cross sectional area in top plan view of the tray. Side walls of the tray, such as substantially vertical side walls, can define the second opening. The tray can be substantially tubular. The tubular tray can have a length (in the direction from the first opening to the second opening) that is smaller than a dimension orthogonal to the length. The one or more supports of the tray can be arranged for holding one or more medical instrument between the first and second openings. The one or more supports can be arranged for locking the instrument(s) in the tray to prevent the instrument(s) from falling out of the tray, e.g. regardless of the orientation of the tray.

Optionally, the first lid includes a tab or rim arranged for being gripped. Optionally, the second lid includes a tab or rim arranged for being gripped. Optionally, the tray includes a tab or rim arranged for being gripped. Optionally, the tab or rim of the tray is positioned eccentrally relative to a center plane passing midway between the first and second openings.

Optionally, one or more of the first lid, the second lid, and the tray includes a centering tab for centering the first lid, the second lid or the tray, respectively.

Optionally, the first lid, the second lid and/or the tray includes a perforation providing an open connection from an inner space of the container to ambient air. The container can including a label closing the perforation.

Optionally, the first and/or second lid includes a transparent window for allowing visual inspection of the instrument(s) in the container without opening the container. Optionally, the first and/or second lid is transparent.

Optionally, the first lid includes one or more recesses or protrusions, arranged for cooperating with one or more corresponding protrusions or recesses, respectively, of a second lid of another container, for stacking the containers.

Optionally, the first and/or second lid includes a geometry arranged for allowing stable positioning on the tray in an upside-down manner. Thus, in a simple manner a decontaminated workspace can be provided for preparing the decontaminated instrument(s).

Optionally, the container is arranged to be closed such that a microbial barrier is formed preventing microbes from entering the inner space. Optionally, the container is arranged to be hermetically closed. Optionally, the container is arranged to maintain a reduced gas pressure inside when closed.

Optionally, the container includes a tamper evidence feature arranged for being in a first state when the reduced gas pressure is present inside the container, and in a second state when ambient pressure is present inside the container.

Optionally, the container includes a machine readable identification.

According to an aspect is provided a decontamination device of the system.

According to an aspect is provided a decontamination device for reprocessing a reusable medical instrument in a container. The container includes a tray and a lid. The tray includes one or more supports for supporting one or more medical instruments. The tray includes an opening for inserting therethrough the one or more medical instruments into an inner space of the tray. The lid is arranged for closing the opening. The decontamination device includes an entrance for receiving the container into the decontamination device. The decontamination device includes a container handler arranged for holding the container in the decontamination device. The decontamination device includes a decontamination unit arranged for decontaminating the tray, the lid and the medical instrument. The decontamination device includes an exit for removing the closed container containing the decontaminated medical instrument from the decontamination device. The container handler is arranged for holding the lid positioned away from the opening while decontaminating. The container handler is arranged for closing the container by closing the lid onto the tray after decontamination.

The container is preferably such that when positioned in a position for normal use (e.g. placed on a table top) the opening extends substantially horizontally. Preferably, the medical instruments are positioned inside the container in a lying down position, when the container is in the position for normal use. Preferably, the medical instruments are positioned (substantially) horizontally in the container when the container is in the position for normal use. Optionally, the container handler is arranged for maintaining the tray in a position with the opening extending in an upright plane, and optionally the further opening extending in a further upright plane, while decontaminating.

Optionally, the decontamination device is arranged to receive the container while the container is in a non-sealed state.

Optionally, the decontamination device includes a first chamber and a second chamber. The container handler can be arranged for transporting the container from the first chamber to the second chamber. The decontamination device can be arranged for performing a first decontaminating in the first chamber and a second decontaminating in the second chamber.

Optionally, the first chamber and the second chamber are positioned with their respective main directions of extension substantially parallel.

Optionally, the decontamination device is arranged for closing the container while moving it from the first chamber to the second chamber.

Optionally, the decontamination device includes a labelling unit arranged for applying a label to the container. Optionally, the labelling unit is arranged for closing a perforation of the container with the label, in the non-sealed state the perforation of the container providing an open connection from an inner space of the container to ambient air.

Optionally, the decontamination device is arranged for receiving a container including a further lid, the tray having a further opening, preferably opposite the first opening. The container handler can be arranged for holding the further lid positioned away from the further opening while decontaminating. The container handler can be arranged for closing the container by closing the further lid onto the tray after decontamination.

Optionally, The entrance is arranged for receiving the container while the lid, and the optional further lid, is closed onto the tray.

Optionally, the container handler is arranged for removing the lid from the opening, and optionally removing the further lid from the further opening, prior to decontamination.

Optionally, the container handler is arranged for gripping the container by the tray, by the lid, and by the optional further lid. Optionally, the container handler is arranged for griping a tab or rim of the lid. Optionally, the container handler is arranged for griping a tab or rim of the further lid. Optionally, the container handler is arranged for griping a tab or rim of the tray.

Optionally, the decontamination unit is arranged for one or more of rinsing, washing, disinfecting, sterilizing, and drying. The washing can include washing at a low temperature, e.g. at about 37° C., to avoid coagulation of blood. Alternatively, or additionally, the washing can include washing at a high temperature, e.g. at 50-100° C., e.g. at about 73° C. The washing can include using water, e.g. using a detergent. Disinfecting can be performed using a disinfectant. Sterilizing can be performed using steam. Preferably, sterilizing is performed using a gaseous sterilizer such as ozone. Drying can be performed using, e.g. hot, air. It is possible that the decontaminating steps are performed in the two chambers, or in more chambers. For example, each decontaminating step can be performed in a dedicated chamber. The decontamination device can include one or more of a rinsing chamber, a washing chamber, a disinfecting chamber, a drying chamber, and a sterilizing chamber. The decontamination device can include a first washing chamber and a second washing chamber. The first washing chamber can be arranged for washing at the low temperature. The second washing chamber can be arranged for washing at the high temperature.

Optionally, the decontamination device is arranged for closing the container such that a microbial barrier is formed preventing microbes from entering the inner space. Optionally, the decontamination device is arranged for hermetically closing the container. Optionally, the decontamination device includes a pump for reducing a gas pressure inside the container prior to closing the container.

Optionally, the decontamination device includes a reader arranged for reading decontamination instructions from a machine readable identification of the container.

According to an aspect, a method is provided for associating one or more reusable medical instruments with a container. It is for instance possible to associate a predetermined set of instruments with a predetermined container. Using a user interface, e.g. of a decontamination device, e.g. of a decontamination system, as described above, a record can be stored in a memory including data representative of the set of instruments and the container. The record can also include data representative of a machine readable identification of the container. The container can also include a human readable identifier, such as a name, a number, a code, a color, a drawing, or the like. It is also possible to associate a set of instruments with a predetermined type of container. For instance, a number of, e.g. five, types of container can be predefined. The container types can e.g. be recognizable by their human readable identifier, such as a colored label.

Using the user interface, processing instructions (such as which decontamination process steps to follow) can be inserted and/or selected. Data representative of the processing instructions can be stored in the record.

Once the medical instrument, or set of medical instruments is associated with a (type of) container, the instrument(s) are intended to remain with that (type of) container. For example. The container including the decontaminated instrument(s) can be taken from the decontamination device, or from storage, and brought to a treatment space. There the decontaminated instrument(s) is (are) taken from the container (e.g. after inspection of the tamper evidence) and used for the procedure. After the procedure, the contaminated instrument(s) is (are) repositioned in the container. The container is presented at the decontamination device. For example, the reader of the decontamination device can determine the machine readable identification of the holder. From the memory the corresponding record is retrieved. The decontamination of the instrument(s) in the container can be performed using the processing instructions in the record. Hence, there is no need for entering processing instructions for the same instrument(s) each time the instrument(s) is (are) presented at the decontamination device.

According to an aspect a method is provided for reprocessing reusable medical instruments in a container. The container includes a tray and a lid. The tray includes one or more supports for supporting one or more medical instruments. The tray includes an opening for inserting therethrough the one or more medical instruments into an inner space of the tray. The lid is arranged for closing the opening. The method includes maintaining the tray in a position with the opening extending in an upright plane while decontaminating.

Optionally, the medical instruments to be decontaminated are maintained in an upright position during decontamination. For generally elongate medical instruments, in the upright position, the main axis of elongation of the instrument is upright, such as substantially vertical. Thus the contact area of the instrument with the supports can be minimized. Especially when using jets during decontamination, and/or when using ultrasonic cleaning, the points of contact will change during decontamination, thus allowing full decontamination of the instrument.

It will be appreciated that any one or more of the above aspects, features and options can be combined. It will be appreciated that any one of the options described in view of one of the aspects can be applied equally to any of the other aspects. It will also be clear that all aspects, features and options described in view of the methods apply equally to the system, device and container, and vice versa.

BRIEF DESCRIPTION OF THE DRAWING

The invention will further be elucidated on the basis of exemplary embodiments which are represented in a drawing. The exemplary embodiments are given by way of non-limitative illustration. It is noted that the figures are only schematic representations of embodiments of the invention that are given by way of non-limiting example.

In the drawing.

DETAILED DESCRIPTION

Figure 1:
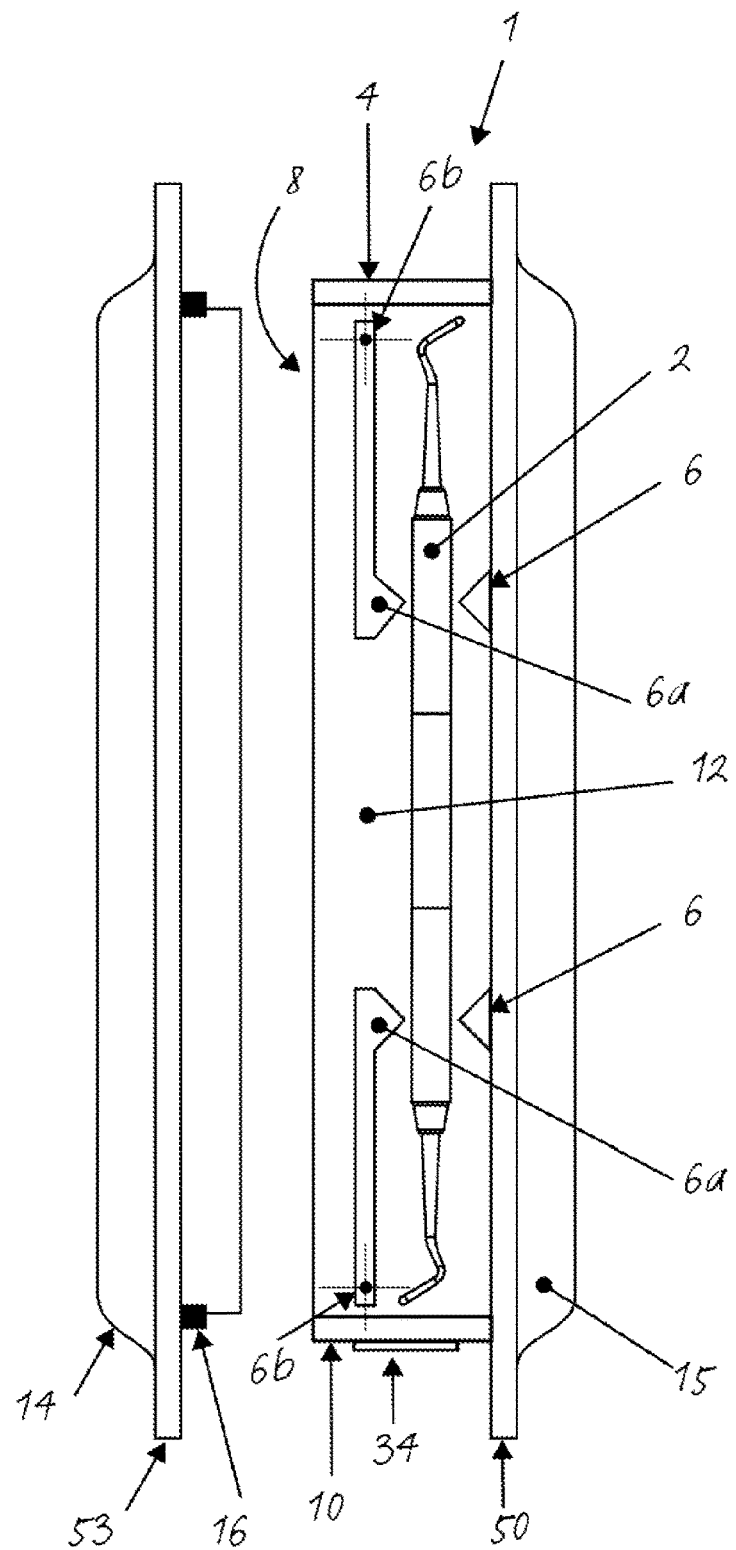
FIG. 1 shows an example of a container.

FIG. 1 shows a schematic drawing of an example of a reprocessing container 1 for holding a reusable medical instrument 2. In the example of FIG. 1 the container includes a tray 4. The tray includes supports 6 for supporting the medical instrument 2 or a plurality of medical instruments 2. Here the supports 6 include movable supports 6a arranged to be moved in an opened position for inserting the instrument 2 and in a closed position for preventing the medical instrument from falling out of the tray, regardless of the orientation of the tray. In this example, the movable supports 6a are pivotally mounted to the tray 4 at pivot points 6b. The tray includes a first opening 8. Here the first opening 8 extends over the entire area formed by the inner surface of the circumferential wall 10 of the tray 4. Thus, in this example, the first opening 8 spans substantially the entire cross sectional area in top plan view of the tray 4. Thus, the instrument 2 or instruments 2, can easily be placed in an inner space 12 of the tray through the first opening 8. In this example, the tray 4 further includes a bottom 15. When used for inserting medical instruments 2 into the container, and/or taking medical instruments 2 from the container, the container 1 will normally be placed with the bottom 15 resting on a carrier surface, such as a counter top or table top. Here the bottom 15 is integral with the circumferential wall 10.

Here, the container 1 includes a first lid 14. The first lid is arranged for closing the first opening 8. In this example, the first lid 14 includes a first circumferential seal 16. In normal use, with the bottom 15 facing downwards, opening the first lid 14 allows easy access to the medical instrument(s) 2 inside the container 1 via the first opening 8, which then extends on an upper side of the tray 4.

Figure 2:
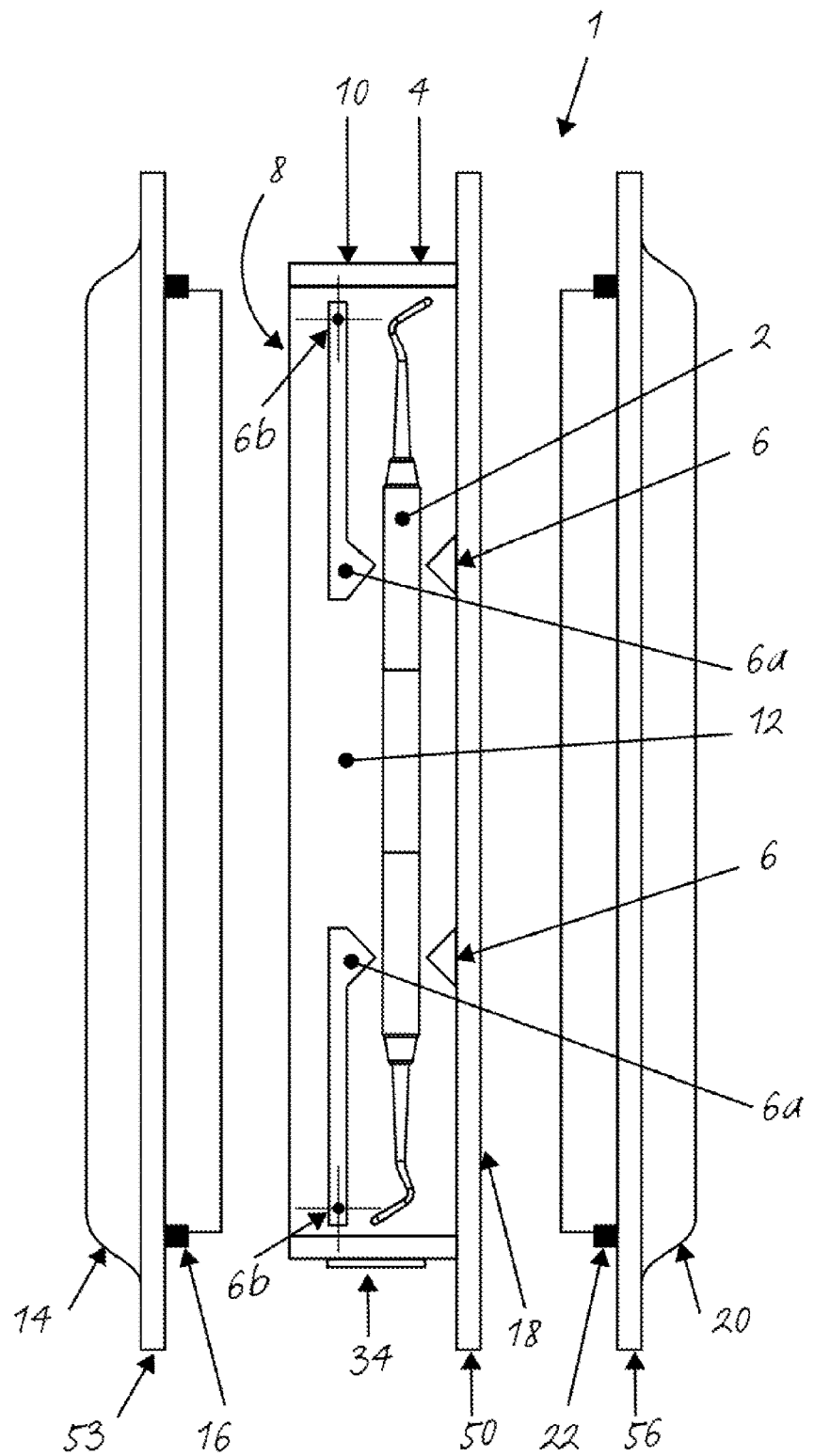
FIG. 2 shows an example of a container.
Figure 3:
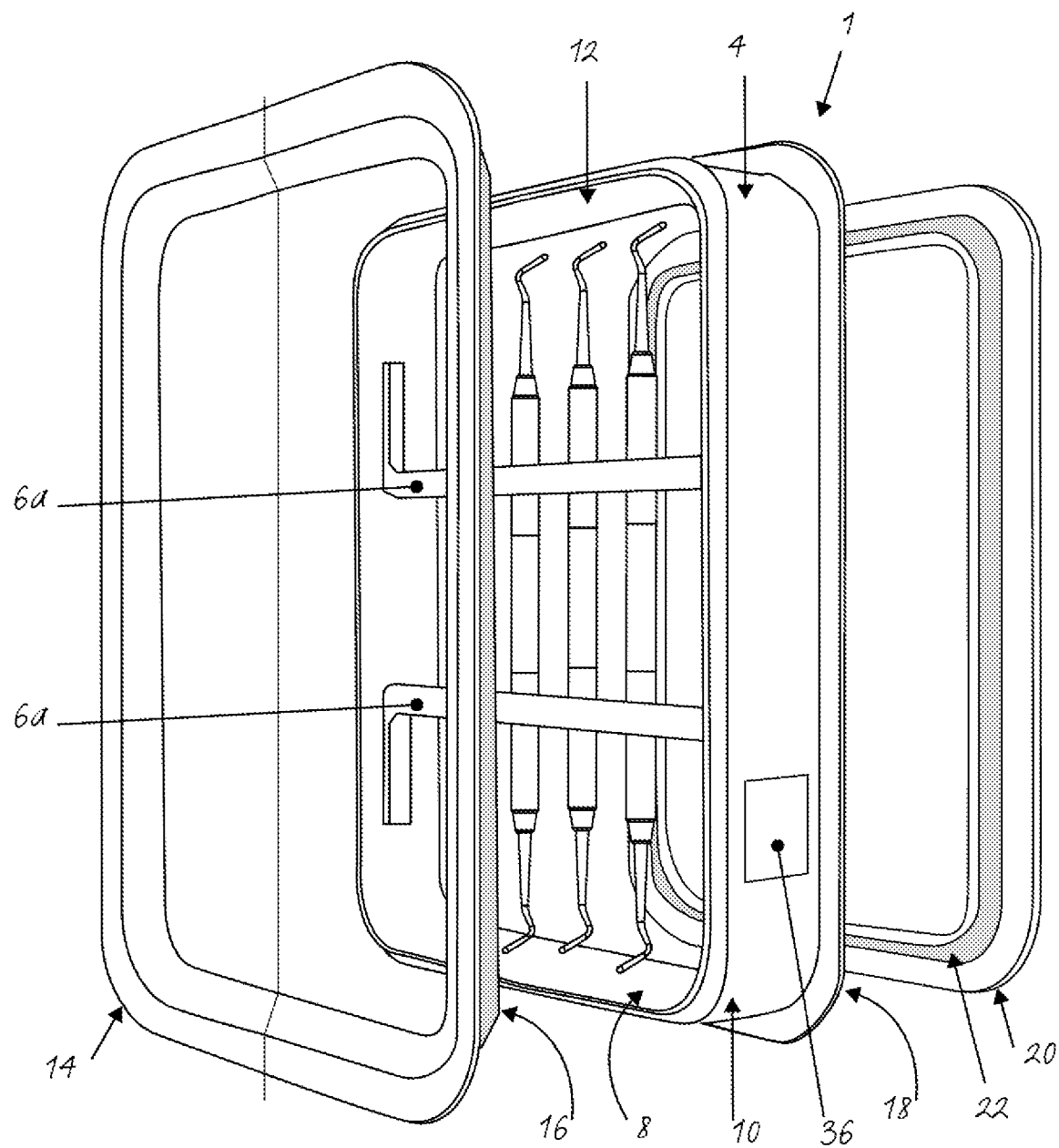
FIG. 3 shows an example of an exploded view of a container.

FIG. 2 shows a schematic drawing of an example of a reprocessing container 1 for holding a reusable medical instrument 2. FIG. 3 shows an isometric exploded view of the container 1 of FIG. 2. In this example the container includes a tray 4. The tray includes supports 6 for supporting the medical instrument 2 or a plurality of medical instruments 2. Here the supports 6 includes movable supports 6a for preventing the medical instrument from falling out of the tray, regardless of the orientation of the tray. In this example, the movable supports 6*a* are pivotally mounted to the tray 4 at pivot points 6*b*. The tray includes a first opening 8. Here the first opening 8 extends over the entire area formed by the inner surface of the circumferential wall 10 of the tray 4. Thus, in this example, the first opening 8 spans substantially the entire cross sectional area in top plan view of the tray 4. Thus, the instrument 2 or instruments 2, can easily be placed in an inner space 12 of the tray through the first opening 8.

Here, the container 1 includes a first lid 14. The first lid is arranged for closing the first opening 8. In this example, the first lid 14 includes a first circumferential seal 16.

In the example of FIG. 2, the tray 4 includes a second opening 18. Here the second opening 18 extends over the entire area formed by the inner surface of the circumferential wall 10 of the tray 4. Thus, in this example, the second opening 18 spans substantially the entire cross sectional area in top plan view of the tray 4. Here, the container 1 includes a second lid 20. The second lid 20 is arranged for closing the second opening 18. In this example, the second lid 20 includes a second circumferential seal 22.

When used for inserting medical instruments 2 into the container, and/or taking medical instruments 2 from the container, the container 1 will normally be placed with the second lid 20 resting on a carrier surface, such as a counter top or table top. The second lid 20 then acts as a bottom of the container 1.

In normal use, with the second lid 20 facing downwards, opening the first lid 14 allows easy access to the medical instrument(s) 2 inside the container 1 via the first opening 8, which then extends on an upper side of the tray 4.

In the examples of FIGS. 1 and 2, the container 1 can include a machine readable identification 34, here a radiofrequency identification, RFID. In these examples, the container 1 can also include a human readable identification 36, here a label.

Figure 4:
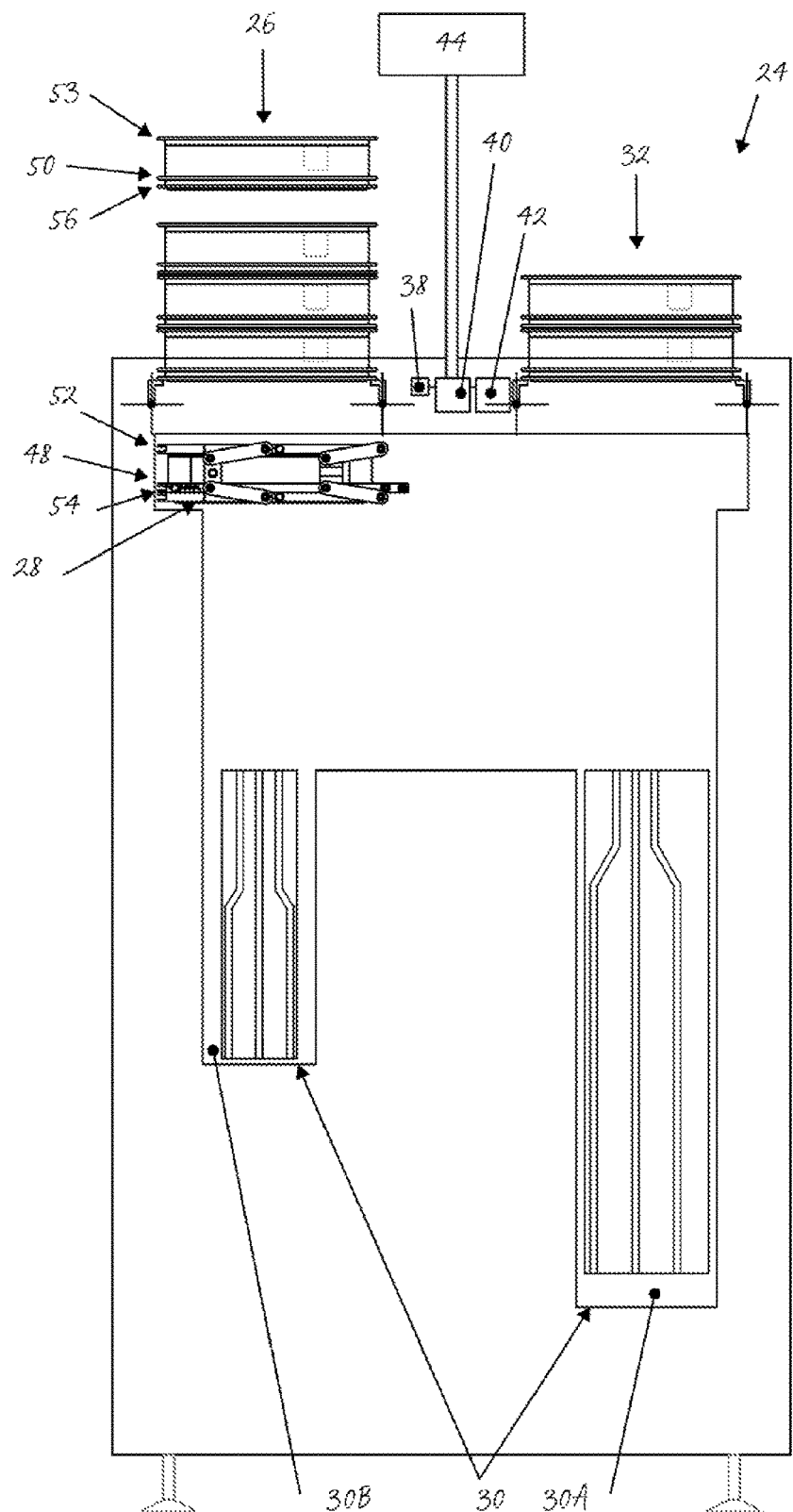
FIG. 4 shows an example of a decontamination device.

FIG. 4 shows a schematic representation of an example of a decontamination device 24. The decontamination device 24 includes an entrance 26. The entrance 26 is arranged for inserting a container 1 into the decontamination device 24. As will be described below, the decontamination device can be used with a container 1 as described in view of FIG. 1 and/or a container 1 as described in view of FIGS. 2 and 3. It will be appreciated that the decontamination device 24 in combination with one or more containers 1 forms a system for reprocessing a reusable medical instrument 2.

The decontamination device 24 includes a container handler 28 arranged for holding the container 1 in the decontamination device. The decontamination device 24 includes a decontamination unit 30 arranged for decontaminating the container 1 and the medical instrument 2. The decontamination device includes an exit 32 for removing the closed container 1 containing the decontaminated medical instrument 2 from the decontamination device.

In this example, the decontamination device 24 includes a reader 38 for reading the machine readable identification 34.

Here, the decontamination device 24 includes a processor 40. The processor 40 is communicatively connected with a memory 42. The processor 40 is communicatively connected with a user interface 44.

In this example the decontamination unit 30 includes a first chamber 30A and a second chamber 30B.

The decontamination device 24 as described thus far can be used as follows with reference to FIG. 4 and FIGS. 5*a*-5*g*.

A container 1 and a medical instrument 2 to be decontaminated are presented at the decontamination device 24. In this example, the contaminated medical instrument 2 is included inside the inner space 12. Here, the container 1 is closed. The container 1 is presented at the entrance 26. The reader 38 reads the identification 34 of the container. In this example, a stack of containers 1 is presented at the entrance 26 (see FIG. 4). Hence, a next container including an instrument 2 to be decontaminated can be placed on top of the stack and wait to be processed by the decontamination device 24.

In this example, the processor 40 retrieves from the memory 42 a record associated with the identification 34 of the container 1. In this example, the record includes data representative of processing instructions for the decontamination of the container 1. It is possible that data representative of the processing instructions is displayed on the user interface 44. For instance, the user interface may display a cleaning cycle as retrieved from the record. It will be appreciated that it is possible that the user interface 44 allows manual manipulation of the processing instructions. It is also possible that the processor 40 does not retrieve processing instructions from the memory 42, and that the user interface 44 prompts the user to enter processing instructions for the container.

Figure 5A:
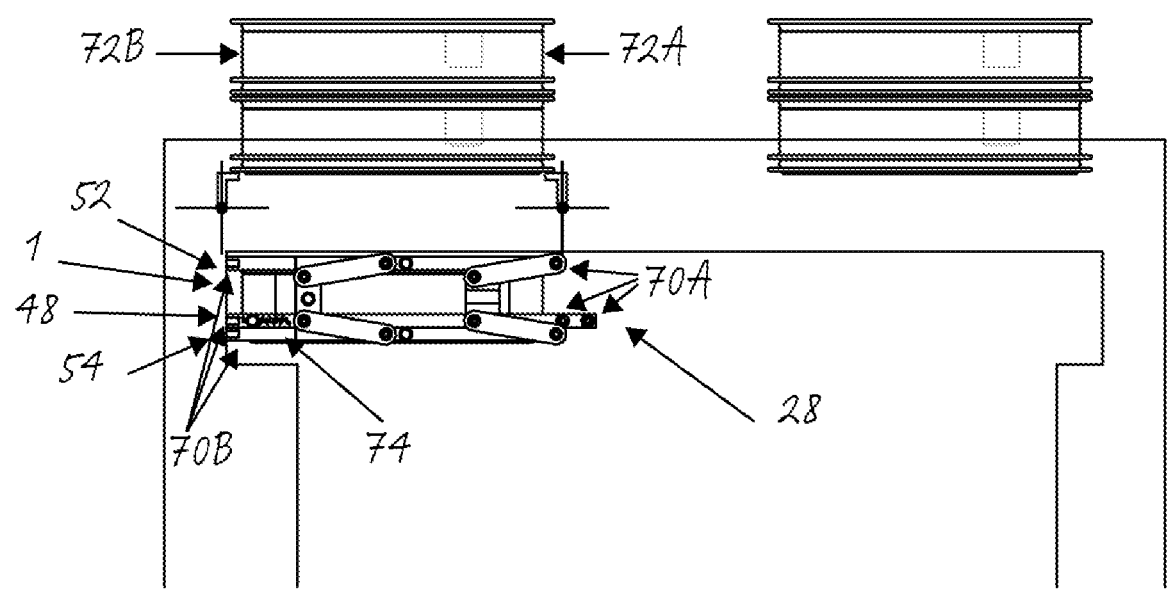
FIGS. 5a-5g show examples of processing steps in an exemplary decontamination device.
Figure 5B:
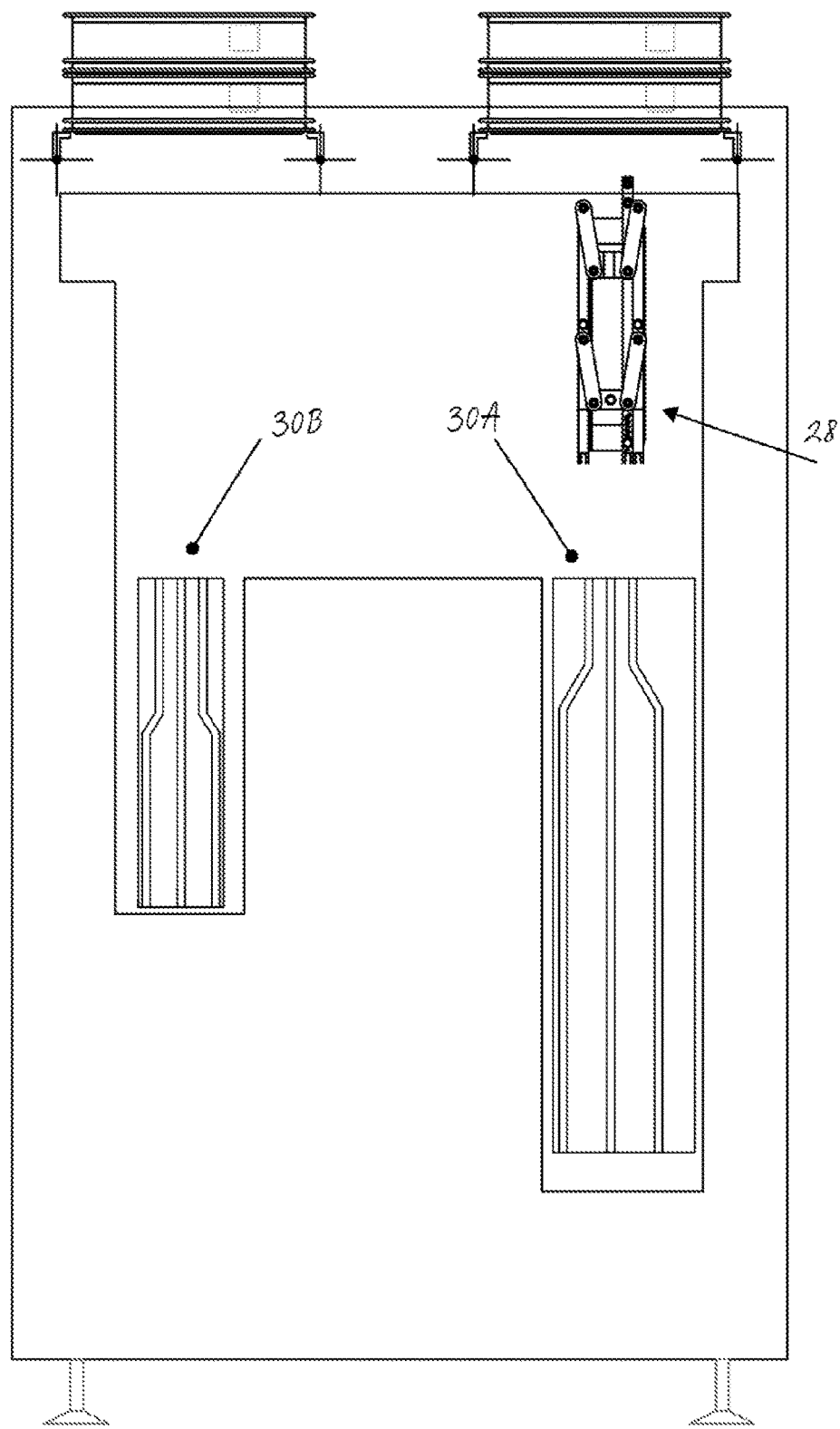

The container 1 at the bottom of the stack is engaged by the container handler 28 (see FIG. 5*a*). In this example, the container handler 28 includes a first jaw 48 arranged for engaging the tray 4, here at a rim 50 of the tray 4. In this example, the container handler 28 also includes a second jaw 52 arranged for engaging the first lid 14, here at a rim 53 of the first lid 14. The container handler 28 can include a third jaw 54 arranged for engaging the second lid 20, e.g. at a rim 56 of the second lid. It will be appreciated that if the decontamination device is arranged for solely processing containers as described in view of FIG. 1, the third jaw 54 may be omitted.

In this example, the jaws 48, 52, 54 include grooved side members 70A, 70B arranged for engaging a front side 72A and a rear side 72B of the rims 50, 53, 56, respectively. Here the grooved side members 70B are biased by a resilient element 74, such as a spring, to close around the respective rim. By moving the grooved side members 70B against the biasing force, a distance between the grooved side members 70A, 70B can be enlarged for gripping the respective rim.

In this example, the container 1 is moved to the first chamber 30A while the container 1 is maintained in its closed state. Here the container handler 28 moves the container 1 from the bottom of the stack horizontally to above the second chamber 30A. Then the container handler 28 tilts the container 1 such that the openings 8, 18 (although still closed by the lids 14, 20) extend in a vertical plane (see FIG. 5*b*). It will be appreciated that a deviation from exactly vertical is possible. Next, the container 1 is lowered into the first chamber 30A. It will be appreciated that the generally elongate medical instruments 2 are positioned in an upright position, with their longitudinal axis substantially vertical.

Figure 5C:
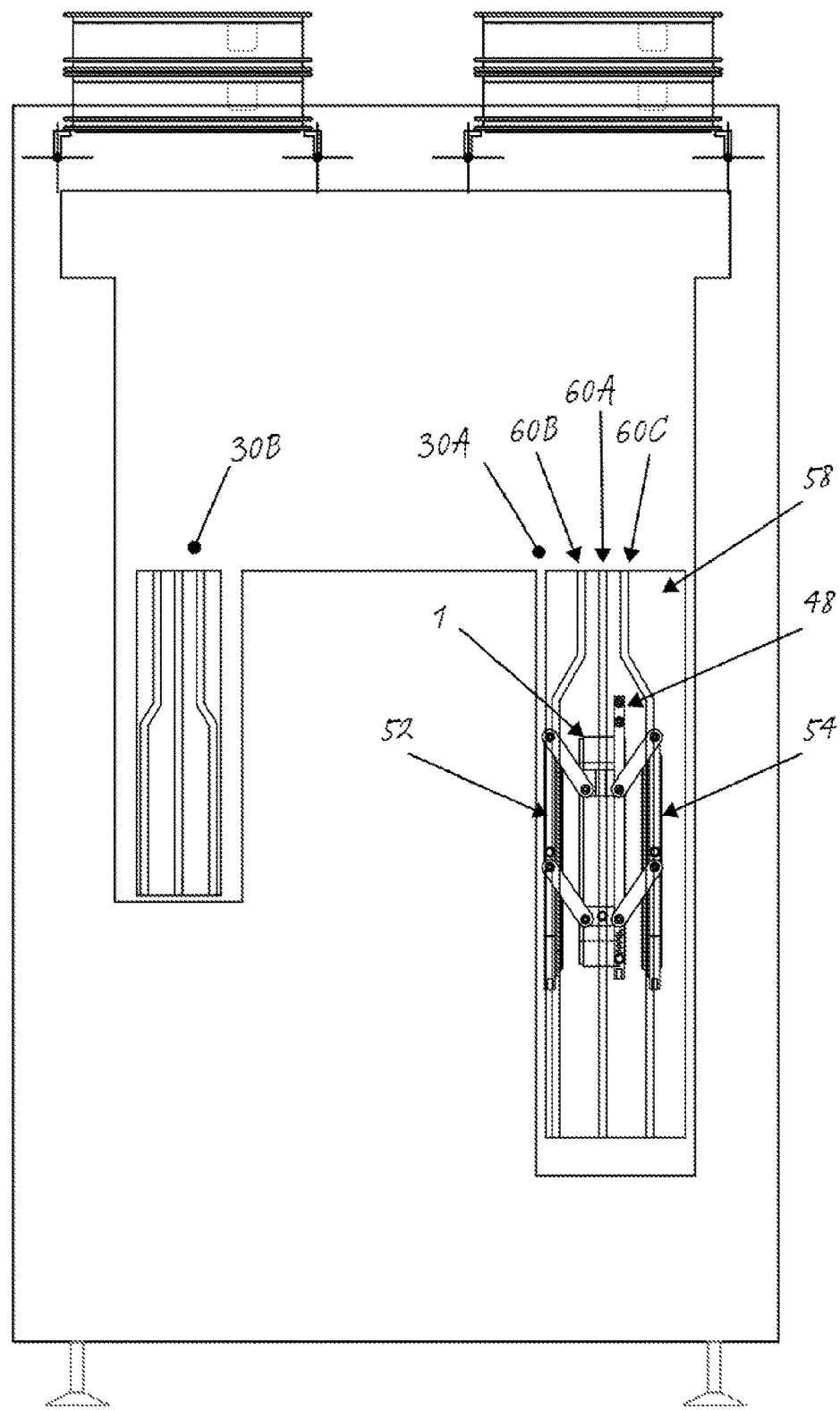
Figure 5D:
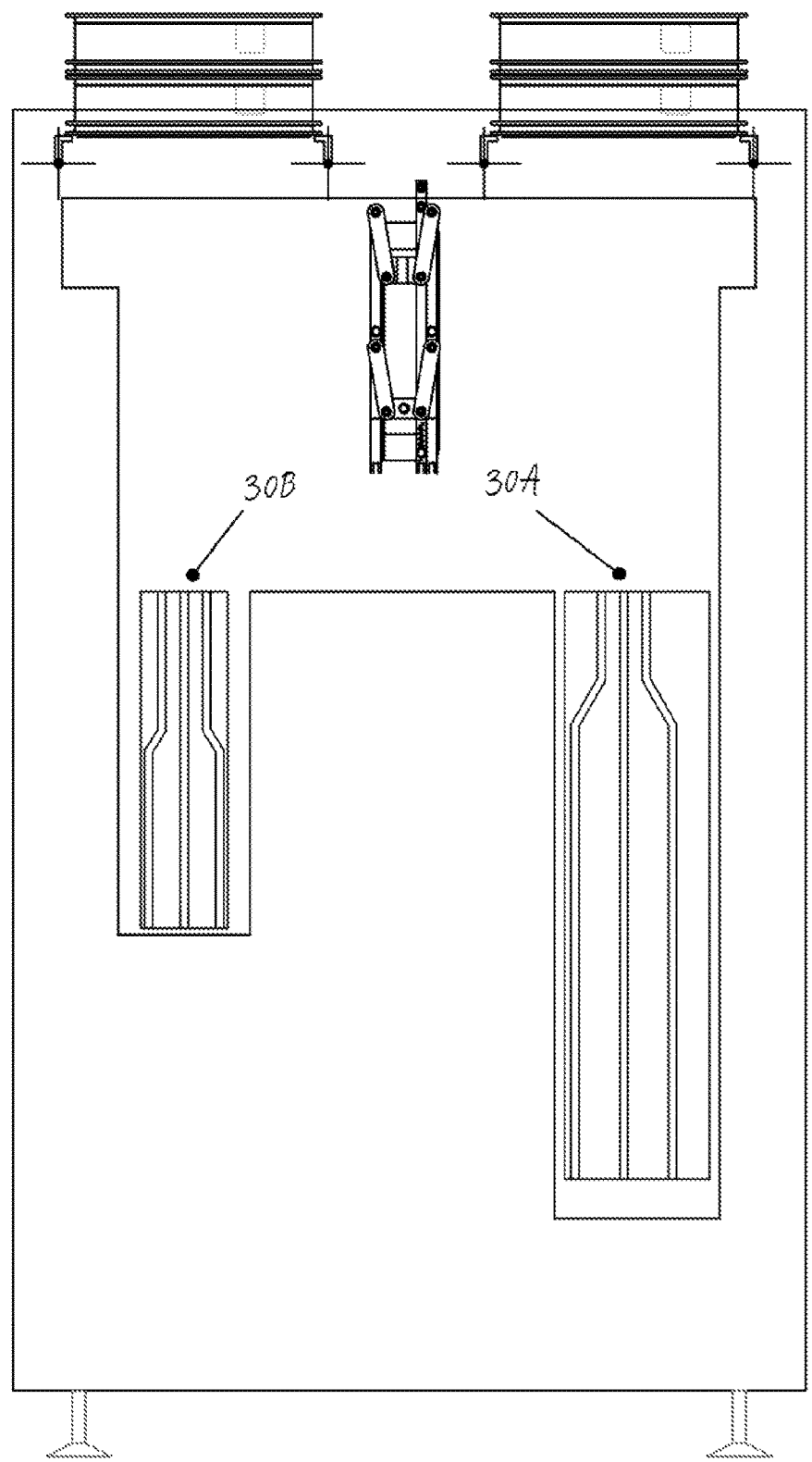
Figure 5E:
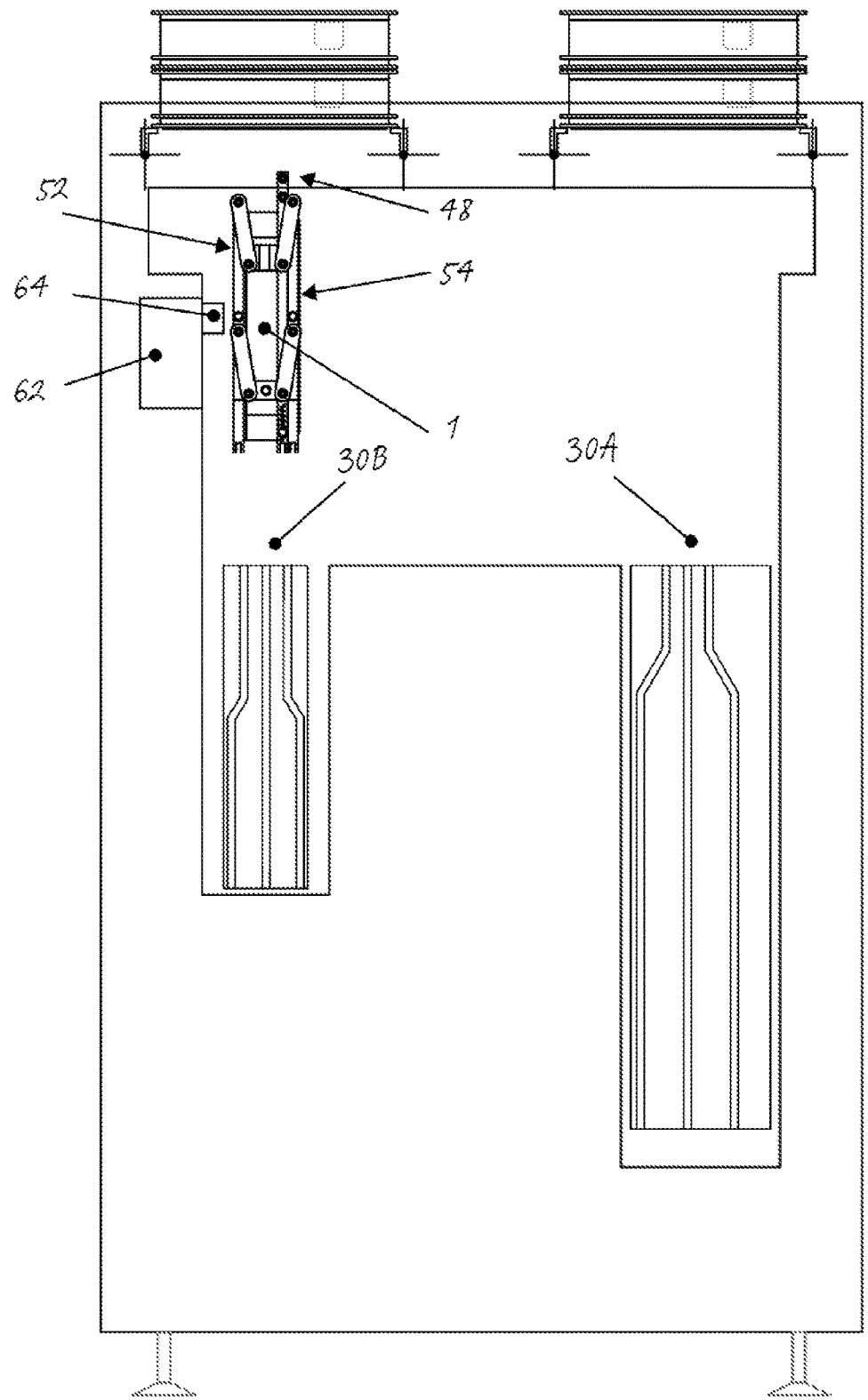

Once in the first chamber (or while or before entering the first chamber) the first lid 14 is moved away from the first opening 8 by the second jaw 52 and the second lid 20 is moved away from the second opening 18 by the third jaw 54 (see FIG. 5*c*). In this example, walls 58 of the first chamber 30A include guide grooves 60A, 60B, 60C. The first guide groove 60A guides the first jaw 48 when entering the first chamber 30A. Here, the first guide groove 60A guides the first jaw 48 along a straight line. The second guide groove 60B guides the second jaw 52 when entering the first chamber 30A. Here, the second guide groove 60B guides the second jaw 52 along a curved line. The curved line of the second guide groove 60B moves the first lid 14 away from the first opening 8, effectively opening the first opening 8. The third guide groove 60C guides the third jaw 54 when entering the first chamber 30A. Here, the third guide groove 60C guides the third jaw 54 along a curved line. The curved line of the third guide groove 60C moves the second lid 20 away from the second opening 18, effectively opening the second opening 18.

Now the container 1 is in the first chamber 30A in an opened state. The internal faces of the container, and the contained instrument(s) can be decontaminated. It will be appreciated that in this example, the external faces of the container can also be decontaminated.

In this example, decontamination includes the following process steps. In this example, a first process step is rinsing. For rinsing, jets of a liquid, such as cold water, are directed at the internals of the container 1. During rinsing, the container 1 may be moved up and down relative to the jets to improve rinsing. In this example, a second process step is washing. For washing, in this example the first chamber 30A is filled with a washing liquid to a level that is sufficient for submerging the entire container. During washing, ultrasonic cleaning may be used in the liquid bath in which the container and instruments are submerged. In this example, a third process step is disinfecting. For disinfecting, in this example, jets of a liquid, such as hot water containing a disinfectant, are directed at the internals of the container 1. During disinfecting, the container 1 may be moved up and down relative to the jets. In this example, a fourth process step is drying. For drying, a drying gas, such as hot air, is flown through the opened container.

It will be appreciated that in view of the above process steps, the decontamination device can include one or more nozzles for generating jets, rinsing liquid supply means, washing liquid supply means, disinfection liquid supply means, liquid pumps for feeding the nozzles, liquid pumps for filling the chamber, liquid pumps for emptying the chamber, liquid heating means, gas heating means, blowing means, and an ultrasound transducer.

Figure 6:
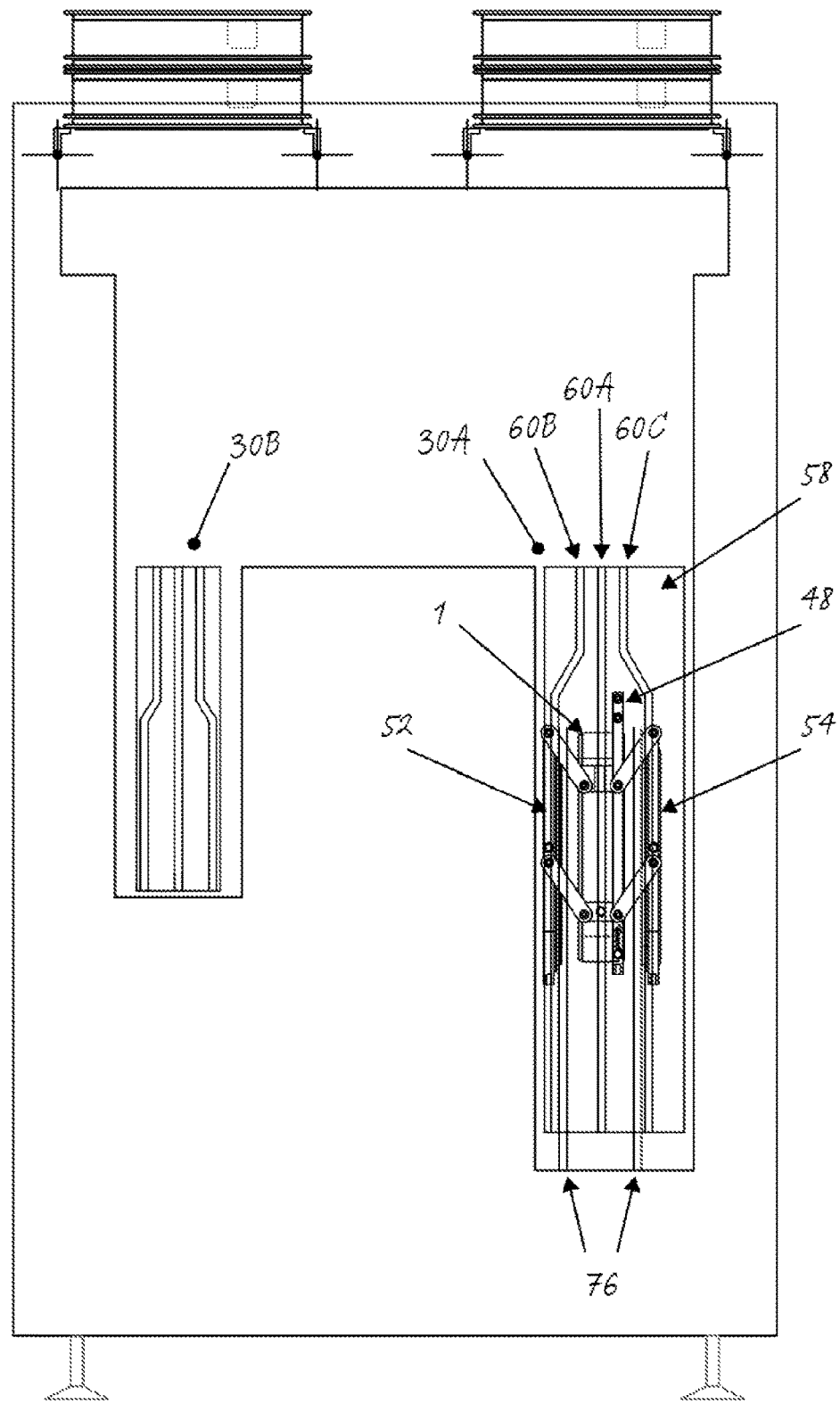
FIG. 6 shows an example of a decontamination device.

The nozzles can be placed on a structure extending from a bottom of the first chamber (see FIG. 6). The structure can be arranged such that the tray 4 passes the structure on one side and the first or second lid passes the structure on an opposite side. Hence, the structure is interposed between the tray and the first or second lid when the container is in its opened state in the first chamber. This allows efficient positioning of the nozzles close to the tray, lid and medical instruments. It will be appreciated that a first such structure can be interposed between the first lid and the tray and a second such structure can be interposed between the second lid and the tray. It is also possible that one or more ultrasound transducers are positioned on the structure(s).

It will be appreciated that the decontamination process may be modified to suit the decontamination needs of the medical instruments included in the container. For example, one or more process steps may be omitted if desired. It is also possible that process parameters, such as liquid temperature, jet pressure, jet duration, ultrasound intensity, ultrasound duration, movement of the container during rinsing, washing, disinfecting and/or drying, gas temperature, etc. may be varied according to need.

In this example after drying the container 1 is removed from the first chamber 30A. Here, during lifting of the container 1 out of the chamber 30A, the guide grooves 60A, 60B, 60C cause the container 1 to be closed again. Thus, the decontaminated closed container is provided at this point. In this example, the container 1 is transported (see FIG. 5d) towards a labelling unit 62 (see FIG. 5e). The labelling unit 62 is arranged for applying a label 64 to the container 1, here to the first lid 14. The label 64 can include human readable indications. The human readable indications can e.g. include information on the decontamination process performed on the (contents of the) container. The information can e.g. include a processing date and/or an expiration date.

Figure 5F:
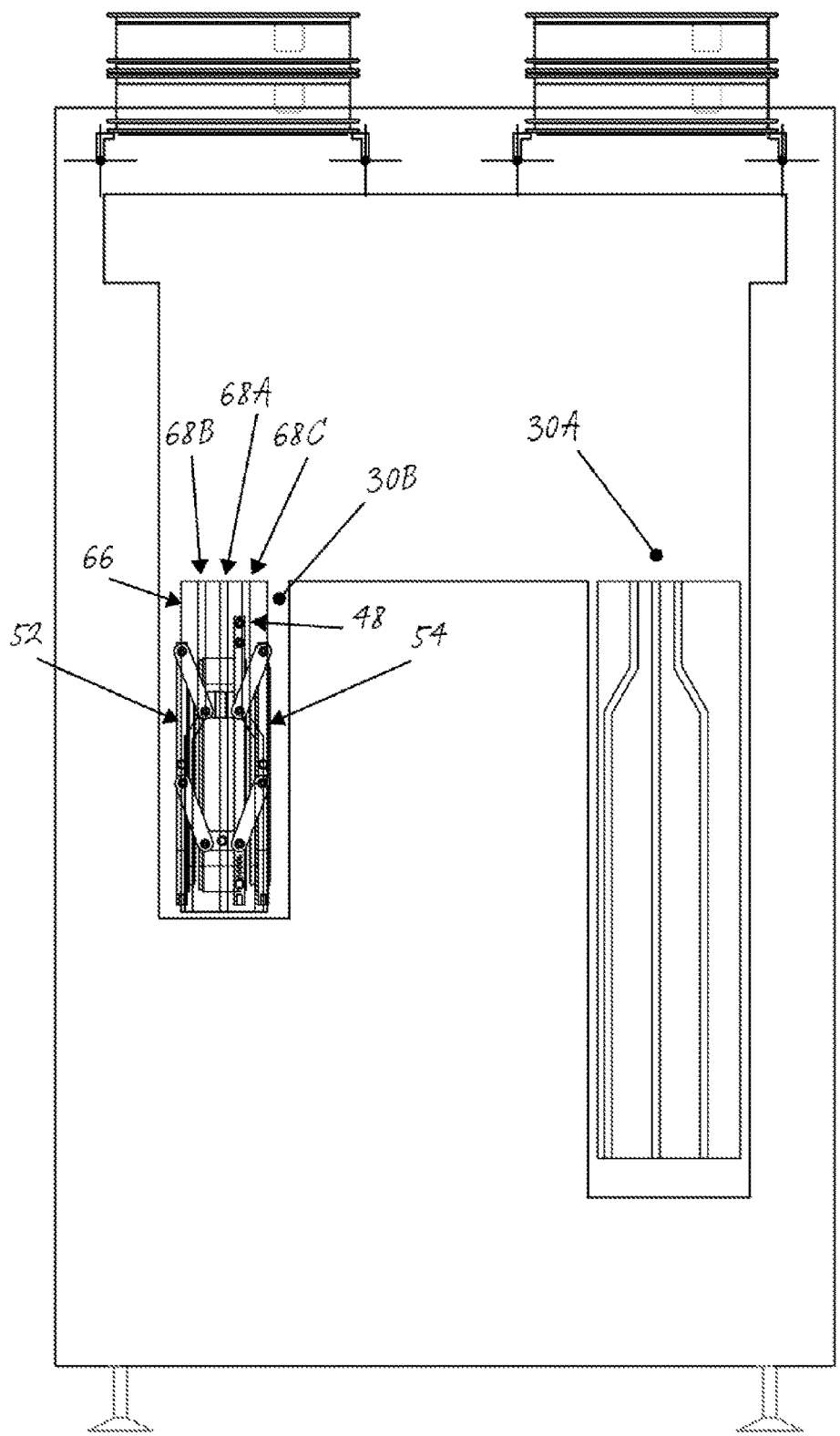
Figure 5G:
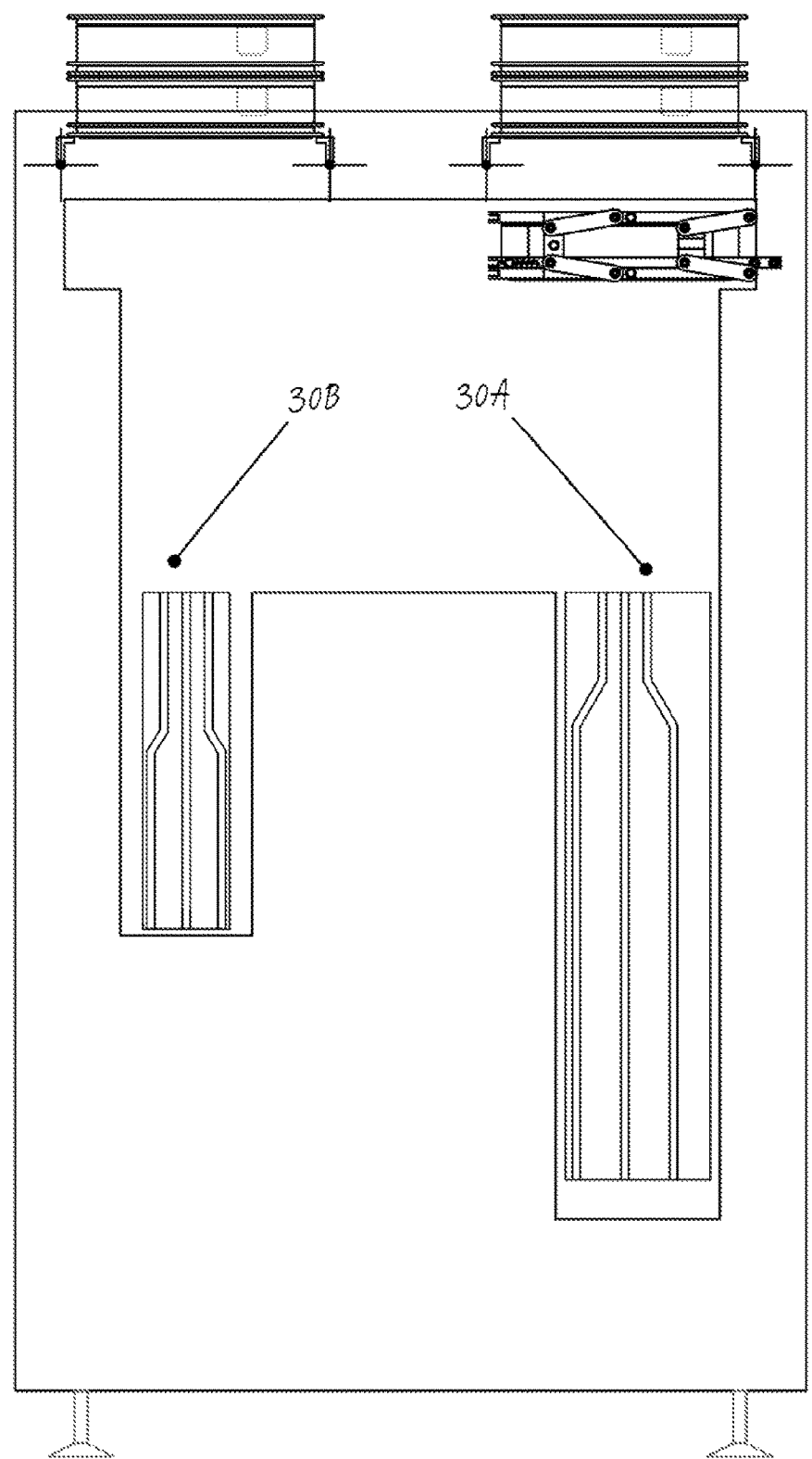

In this example, the container 1 is lowered into the second chamber 30B for performing a further process step (see FIG. 5f). Once in the second chamber (or while or before entering the second chamber) the first lid 14 is moved away from the first opening 8 by the second jaw 52 and the second lid 20 is moved away from the second opening 18 by the third jaw 54. In this example, walls 66 of the second chamber 30B include guide grooves 68A, 68B, 68C. The first guide groove 68A guides the first jaw 48 when entering the second chamber 30B. Here, the first guide groove 68A guides the first jaw 48 along a straight line. The second guide groove 68B guides the second jaw 52 when entering the second chamber 30B. Here, the second guide groove 68B guides the second jaw 52 along a curved line. The curved line of the second guide groove 68B moves the first lid 14 away from the first opening 8, effectively opening the first opening 8. The third guide groove 68C guides the third jaw 54 when entering the second chamber 30B. Here, the third guide groove 68C guides the third jaw 54 along a curved line. The curved line of the third guide groove 68C moves the second lid 20 away from the second opening 18, effectively opening the second opening 18.

In the second chamber 30B in this example, a fifth process step is performed. In this example, the fifth process step is sterilizing. For sterilizing, in this example, the second chamber 30B is filled with a sterilizing gas, e.g. containing ozone. It will be appreciated that information on sterilization can also be included on the label 64. The label may be applied to the container before sterilization or after sterilization.

In this example, a sixth process step is evacuation. Here, the second chamber is evacuated, e.g. to a predetermined pressure below ambient pressure. In this example during lifting of the container 1 in the second chamber 30B, the guide grooves 68A, 68B, 68C cause the container 1 to be closed again. Here, the container is closed inside the second chamber 30B while evacuated. Thus, the closed container includes gas, such as air or a protective gas, below ambient pressure. The container 1 can include an indicator arranged for indicating whether or not the pressure inside the container is below a predetermined threshold pressure. Thus, the sterilized closed container is provided at this point. In this example, the container 1 is transported to the exit 32 (see FIG. 5g). In this example, the container is placed at the bottom of a stack of containers at the exit 32. The container can be retrieved from the exit 32, e.g. manually.

Figure 7:
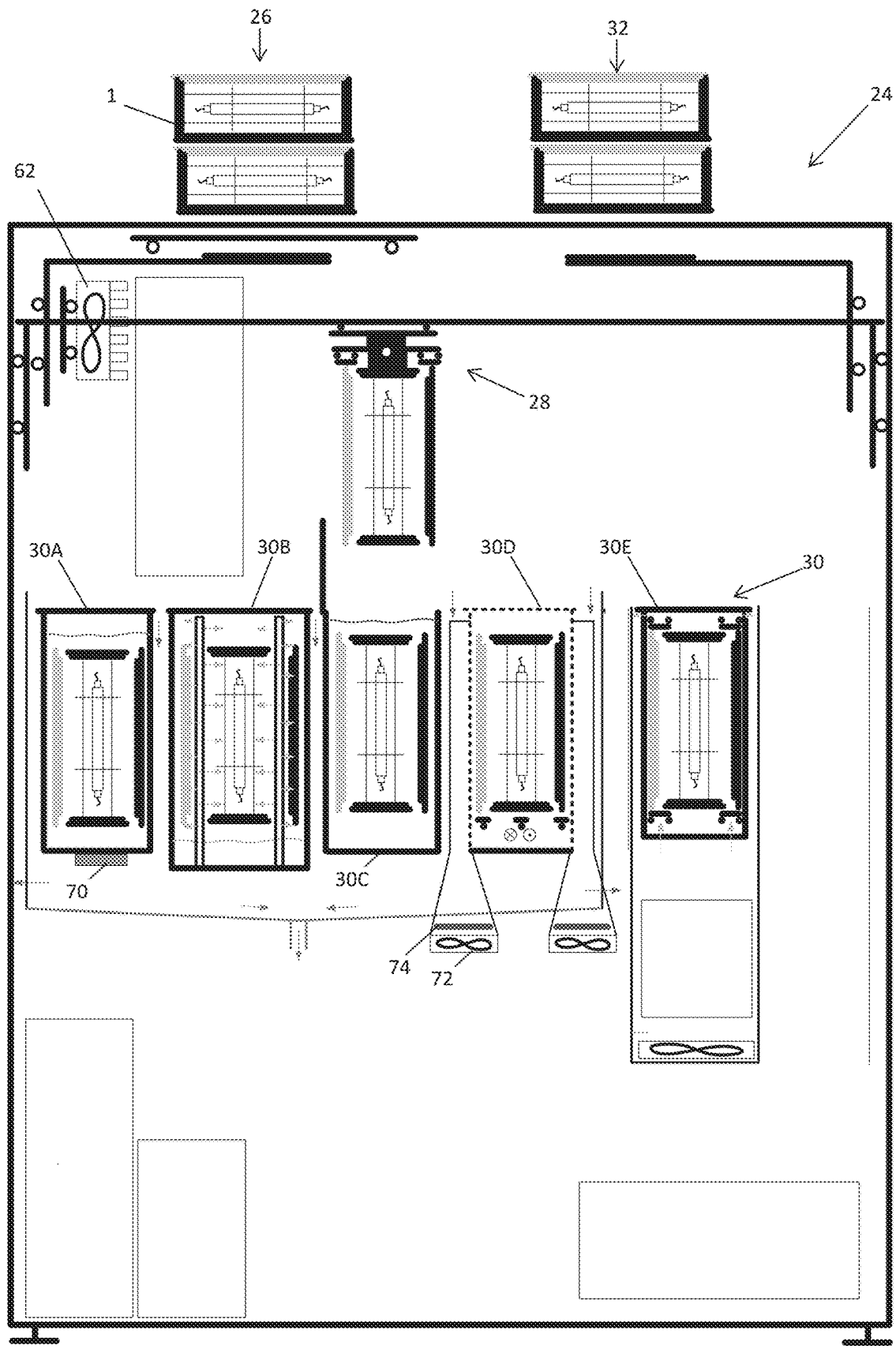
FIG. 7 shows an example of a decontamination device.

FIG. 7 shows a schematic representation of an example of a decontamination device 24. The decontamination device 24 includes an entrance 26. The entrance 26 is arranged for inserting a container 1 into the decontamination device 24. As will be described below, the decontamination device can be used with a container 1 as described in view of FIG. 1 and/or a container 1 as described in view of FIGS. 2 and 3. It will be appreciated that the decontamination device 24 in combination with one or more containers 1 forms a system for reprocessing a reusable medical instrument 2.

The decontamination device 24 includes a container handler 28 arranged for holding the container 1 in the decontamination device. The decontamination device 24 includes a decontamination unit 30 arranged for decontaminating the container 1 and the medical instrument 2. The decontamination device includes an exit 32 for removing the closed container 1 containing the decontaminated medical instrument 2 from the decontamination device.

The decontamination device 24 can include a reader 38 for reading the machine readable identification 34. The decontamination device 24 can include a processor 40. The processor 40 can be communicatively connected with a memory 42. The processor 40 can be communicatively connected with a user interface 44.

In this example the decontamination unit 30 includes a first chamber 30A, a second chamber 30B, a third chamber 30C, a fourth chamber 30D and a fifth chamber 30E. In this example, the first chamber 30A is arranged for washing the medical instrument 2 with a liquid, such as water e.g. including a detergent, at a low temperature, e.g. of 37° C. The first chamber 30A can include ultrasonic means 70 for ultrasonically cleaning the instrument 2. In this example, the second chamber 30B is arranged for washing the medical instrument 2 with a liquid, such as water e.g. including a detergent, at a high temperature, e.g. of 73° C. In this example, the third chamber 30C is arranged for disinfecting the instrument, e.g. at a temperature of 93° C. In this example, the fourth chamber 30D is arranged for drying the instrument 2 and the container 1. Here, the fourth chamber 30D is provided with drying means such as blowers 72 and/or heaters 74. In this example, the fifth chamber 30E is arranged for sterilizing the instruments 2.

In this example, the chambers 30A, 30B, 30C, 30D, 30E are positioned with their respective main planes of extension substantially parallel. Herein, the main plane of extension indicates the directions of the two largest dimensions of the chamber. For example, for a chamber having a length exceeding a width, and the width exceeding a height, the largest dimensions are the length and the width. Hence, the main plane of extension is the plane defined by the length and the width of said chamber. Here the first through fifth chambers 30A, 30B, 30C, 30D, 30E are positioned with their respective main planes of extension substantially parallel, so that they occupy a compact volume. Hence, a compact build of the decontamination device is possible.

The decontamination device 24 as described thus far can be used as follows with reference to FIG. 7.

A container 1 and a medical instrument 2 to be decontaminated are presented at the decontamination device 24. In this example, the contaminated medical instrument 2 is included inside the inner space 12. Here, the container 1 is closed. In this example, the closed container is in a non-sealed state. Here the lid 14 includes a perforation allowing air to enter or exit the inner space of the container. The container 1 is presented at the entrance 26. The reader 38 reads the identification 34 of the container. In this example, a stack of containers 1 is presented at the entrance 26. Hence, a next container including an instrument 2 to be decontaminated can be placed on top of the stack and wait to be processed by the decontamination device 24.

In this example, the processor 40 retrieves from the memory 42 a record associated with the identification 34 of the container 1. In this example, the record includes data representative of processing instructions for the decontamination of the container 1. It is possible that data representative of the processing instructions is displayed on the user interface 44. For instance, the user interface may display a cleaning cycle as retrieved from the record. It will be appreciated that it is possible that the user interface 44 allows manual manipulation of the processing instructions. It is also possible that the processor 40 does not retrieve processing instructions from the memory 42, and that the user interface 44 prompts the user to enter processing instructions for the container.

The container 1 at the bottom of the stack is engaged by the container handler 28. Here the container handler 28 rotates the container 1 from the bottom of the stack from a horizontal orientation to a vertical orientation. It will be appreciated that a deviation from exactly vertical is possible. In this example, the container 1 is moved to above the first chamber 30A while the container 1 is maintained in its closed state. Next, the container 1 is lowered into the first chamber 30A. It will be appreciated that the generally elongate medical instruments 2 are positioned in an upright position, with their longitudinal axis substantially vertical.

Once in the first chamber (or while or before entering the first chamber) the first lid 14 is moved away from the first opening 8 and the second lid 20 is moved away from the second opening 18. Now the container 1 is in the first chamber 30A in an opened state. The internal faces of the container, and the contained instrument(s) can be washed. It will be appreciated that in this example, the external faces of the container can also be washed.

In this example after washing in the first chamber 30A the container 1 is removed from the first chamber 30A. Here, during or before lifting of the container 1 out of the chamber 30A the container 1 is be closed again. Thus, the washed closed container is provided at this point. In this example, the container 1 is transported to above the second chamber 30B. Once in the second chamber 30B (or while or before entering the second chamber) the first lid 14 is moved away from the first opening 8 and the second lid 20 is moved away from the second opening 18. Now the container 1 is in the second chamber 30B in an opened state. The internal faces of the container, and the contained instrument(s) can be washed. It will be appreciated that in this example, the external faces of the container can also be washed.

In this example after washing in the second chamber 30B the container 1 is removed from the second chamber 30B. Here, during or before lifting of the container 1 out of the chamber 30B the container 1 is be closed again. Thus, the washed closed container is provided at this point. In this example, the container 1 is transported to above the third chamber 30C. Once in the third chamber 30C (or while or before entering the third chamber) the first lid 14 is moved away from the first opening 8 and the second lid 20 is moved away from the second opening 18. Now the container 1 is in the third chamber 30C in an opened state. The internal faces of the container, and the contained instrument(s) can be disinfected. It will be appreciated that in this example, the external faces of the container can also be disinfected.

In this example after disinfecting in the third chamber 30C the container 1 is removed from the third chamber 30C. Here, during or before lifting of the container 1 out of the chamber 30C the container 1 is be closed again. Thus, the disinfected closed container is provided at this point. In this example, the container 1 is transported to above the fourth chamber 30D. Once in the fourth chamber 30D (or while or before entering the third chamber) the first lid 14 is moved away from the first opening 8 and the second lid 20 is moved away from the second opening 18. Now the container 1 is in the fourth chamber 30D in an opened state. The internal faces of the container, and the contained instrument(s) can be dried. It will be appreciated that in this example, the external faces of the container can also be dried.

At this point, the container may be moved towards the exit 32 to provide the container containing the medical instruments that have been disinfected but not sterilized. Thereto, the perforation in the lid may be closed with a label as described hereinbelow.

Alternatively, after drying in the fourth chamber 30D the container 1 is removed from the fourth chamber 30D. Here, during or before lifting of the container 1 out of the chamber 30D the container 1 is be closed again. Thus, the dried closed container is provided at this point. In this example, the container 1 is transported to above the fifth chamber 30E. Once in the fifth chamber 30ED (or while or before entering the third chamber) the first lid 14 is moved away from the first opening 8 and the second lid 20 is moved away from the second opening 18. Now the container 1 is in the fifth chamber 30E in an opened state. The internal faces of the container, and the contained instrument(s) can be sterilized. It will be appreciated that in this example, the external faces of the container can also be sterilized. After sterilizing in the fifth chamber 30E the container 1 is removed from the fifth chamber 30E. Here, during or before lifting of the container 1 out of the chamber 30E the container 1 is be closed again. Thus, the sterilized closed container is provided at this point.

The container can be moved towards a labelling unit 62. The labelling unit 62 is arranged for applying a label 64 to the container 1, here to the first lid 14. The label can close the perforation in the lid 14. The label 64 can include human readable indications. The human readable indications can e.g. include information on the decontamination process performed on the (contents of the) container. The information can e.g. include a processing date and/or an expiration date.

In this example, a sixth process step is evacuation. Here, the container may be evacuated, e.g. to a predetermined pressure below ambient pressure, at the labelling unit. Here, the container is closed while evacuated. Thus, the sterilized closed container is provided at this point. In this example, the container 1 is transported to the exit 32. In this example, the container is placed at the bottom of a stack of containers at the exit 32. The container can be retrieved from the exit 32, e.g. manually.

The decontamination method as described above can be used as follows.

In an example, an association is made of a predetermined set of medical instruments with a predetermined container or a predetermined type of container. The predetermined set of instruments can e.g. be a set required for performing a certain procedure on a patient. The predetermined container can be an identifiable container, e.g. a container having a predetermined indicator such as a number, a letter, a code, a color, an icon, a drawing, or the like on an external surface.

The association of the predetermined set of medical instruments with a predetermined container or a predetermined type of container is stored in the memory 42 of the decontamination device, or is stored in a remote memory and is retrievable by the processor 40, e.g. via a communications network, such as an intranet or the internet. The association is stored in a record in memory. The record can include data representative of the set of instruments and the container. The record can also include data representative of a machine readable identification of the container. The record can include processing instructions (such as which decontamination process steps to follow, and using which parameters). It is possible that for a new association, such record can be created using the user interface 44. It is also possible that an existing association can be modified using the user interface 44.

In the above example, when the reader 38 recognizes the container 1, the record can be retrieved from memory and the processing steps for the instruments in that container are automatically loaded in the processor 40. It will be appreciated that it is possible that the user interface provides the possibility of manually modifying or overriding the retrieved processing steps.

Once the medical instrument, or set of medical instruments is associated with a (type of) container, the instrument(s) are intended to remain with that (type of) container. For example. The container including the decontaminated instrument(s) can be taken from the decontamination device, or from storage, and brought to a treatment space. There the decontaminated instrument(s) is (are) taken from the container (e.g after inspection of the tamper evidence) and used for the procedure. After the procedure, the contaminated instrument(s) is (are) repositioned in the container. The container with the contaminated instruments can then be presented at the decontamination device again.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate examples or embodiments, however, alternative embodiments having combinations of all or some of the features described in these separate embodiments are also envisaged.

In the examples, the process steps rinsing, washing, disinfecting and drying are performed in the first chamber, while sterilizing and evacuating is performed in the second chamber. It will be appreciated that it is also possible that the process steps are assigned to the chambers differently. It will be appreciated that it is also possible that all process steps are performed in one single chamber. It is also possible that more than two chambers are used for performing the process steps. It will be appreciated that one or more of the process steps may be omitted in view of the requirements of the medical instrument to be decontaminated.

Herein, the invention is described with reference to specific examples of embodiments of the invention. It will, however, be evident that various modifications, variations, alternatives and changes may be made therein, without departing from the essence of the invention. For the purpose of clarity and a concise description features are described herein as part of the same or separate embodiments, however, alternative embodiments having combinations of all or some of the features described in these separate embodiments are also envisaged and understood to fall within the framework of the invention as outlined by the claims. The specifications, figures and examples are, accordingly, to be regarded in an illustrative sense rather than in a restrictive sense. The invention is intended to embrace all alternatives, modifications and variations which fall within the spirit and scope of the appended claims. Further, many of the elements that are described are functional entities that may be implemented as discrete or distributed components or in conjunction with other components, in any suitable combination and location.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A method for reprocessing a reusable medical instrument, including:
    providing a container including a tray and a lid, the tray including one or more supports supporting the medical instrument, the tray having an opening for inserting therethrough the medical instrument into an inner space of the tray, and the lid being arranged for hermetically closing the opening;
    inserting the container into a decontamination device;
    inside the decontamination device decontaminating the tray, the lid and the medical instrument while the lid is positioned away from the opening;
    inside the decontamination device, a container handler of the decontamination device hermetically closing the container by closing the lid onto the tray for closing the opening;
    reducing gas pressure inside the container prior to closing the container and maintaining said reduced gas pressure inside the container after removing the closed container from the decontamination device; and
    removing the closed container containing the decontaminated medical instrument from the decontamination device.

2. The method of claim 1, including maintaining the tray in an upright position with the opening extending in an upright plane, while decontaminating.

3. The method of claim 1, wherein the container is inserted into the decontamination device while the container is in a non-sealed state.

4. The method of claim 1, wherein during the step of decontaminating the container is subsequently held in a first chamber and a second chamber.

5. The method of claim 4, wherein the first chamber and the second chamber are positioned with their respective main planes of extension substantially parallel.

6. The method of claim 4, wherein the container is closed while being moved from the first chamber to the second chamber.

7. The method of claim 1, including inside the decontamination device applying a label to the container.

8. The method of claim 3, wherein in the non-sealed state a perforation of the lid and/or tray provides an open connection from an inner space of the container to ambient air.

9. The method of claim 8, including closing the perforation with a label while the container is inside the decontamination device.

10. The method of claim 1, wherein the container includes a further lid, the tray having a further opening, preferably opposite the first opening, the method including
    inside the decontamination device decontaminating the tray, the lid, the further lid and the medical instrument while the lid is positioned away from the opening and the further lid is positioned away from the further opening; and
    inside the decontamination device, the container handler closing the lid onto the tray for closing the opening, and closing the further lid onto the tray for closing the further opening.

11. The method of claim 1, wherein the step of inserting includes inserting the container into the decontamination device while the lid is closed onto the tray.

12. The method of claim 11, including inside the decontamination device removing the lid from the opening.

13. The method of claim 1, including the container handler gripping the container by the tray and by the lid.

14. The method of claim 1, wherein the decontaminating includes one or more of rinsing, washing, disinfecting, sterilizing, and drying.

15. The method of claim 14, including performing washing in a first chamber of the decontamination device, and performing sterilizing in a second chamber of the decontamination device.

16. The method of claim 1, wherein the step of closing includes closing the container such that a microbial barrier is formed preventing microbes from entering the inner space.

17. The method of claim 1, including the decontamination device reading decontamination instructions from an identification of the container.

18. The method of claim 10, wherein the step of inserting includes inserting the container into the decontamination device while the further lid is closed onto the tray, removing the lid from the opening inside the decontamination device.

* * * * *